United States Patent
Hageman et al.

(10) Patent No.: US 7,754,686 B2
(45) Date of Patent: Jul. 13, 2010

(54) STABILIZED FGF FORMULATIONS CONTAINING REDUCING AGENTS

(75) Inventors: Robert V. Hageman, Oakland, CA (US); Bret A. Shirley, Concord, CA (US); Kamaljit K. Bajwa, Danville, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 2629 days.

(21) Appl. No.: 09/944,930

(22) Filed: Aug. 31, 2001

(65) Prior Publication Data

US 2008/0293624 A1    Nov. 27, 2008

Related U.S. Application Data

(60) Provisional application No. 60/229,238, filed on Aug. 31, 2000.

(51) Int. Cl.
  *A61K 38/16*   (2006.01)
  *A61K 38/18*   (2006.01)
  *C07K 14/435*  (2006.01)
  *C07K 14/50*   (2006.01)

(52) U.S. Cl. .......................... 514/12; 530/350

(58) Field of Classification Search .................. None
  See application file for complete search history.

(56) References Cited

U.S. PATENT DOCUMENTS

| | | | |
|---|---|---|---|
| 4,100,150 A | 7/1978 | Cartwright | |
| 4,992,271 A | 2/1991 | Hanisch et al. | |
| 5,037,644 A | 8/1991 | Shaked et al. | |
| 5,128,321 A | 7/1992 | Murray et al. | |
| 5,175,147 A | 12/1992 | Folkman et al. | |
| 5,217,954 A | 6/1993 | Foster et al. | |
| 5,310,728 A | 5/1994 | Shimizu et al. | |
| 5,314,872 A | 5/1994 | Kato et al. | |
| 5,348,941 A | 9/1994 | Middaugh et al. | |
| 5,401,721 A | 3/1995 | Folkman et al. | |
| 5,474,982 A | 12/1995 | Murray et al. | |
| 5,510,327 A | 4/1996 | Hayasaka et al. | |
| 5,714,458 A | 2/1998 | Adami et al. | |
| 6,165,981 A * | 12/2000 | Flaa et al. | ............ 514/21 |

FOREIGN PATENT DOCUMENTS

| WO | WO 92/01442 A1 | 2/1992 |
|---|---|---|
| WO | WO 95/07686 | 3/1995 |
| WO | WO 00/21548 | 4/2000 |

OTHER PUBLICATIONS

Akers, M.J., "Antioxidants in Pharmaceutical Products," *Journal of Parenteral Science and Technology*, Sep.-Oct. 1982, pp. 222-228, vol. 36(5).

Beltagy, Y.A., et al., "Antioxidants in Purification, Stabilization, and Formulation of the Antineoplastic Agent 6-Selenoguanosine," *Journal of Pharmaceutical Sciences*. Oct. 1980, pp. 1168-1170, vol. 69(10), American Pharmaceutical Association, USA.

* cited by examiner

*Primary Examiner*—Christine J Saoud
*Assistant Examiner*—Jon M Lockard
(74) *Attorney, Agent, or Firm*—Alston & Bird LLP

(57) ABSTRACT

Stabilized FGF compositions are provided. The compositions comprise FGF or variant thereof and at least one reducing agent in an amount sufficient to inhibit FGF oxidation. Methods for increasing stability of FGF or variant thereof in a liquid or lyophilized composition and for increasing storage stability of such a composition are also provided.

13 Claims, 7 Drawing Sheets

SEQUENCE LISTING

```
<160> NUMBER OF SEQ ID NOS: 8

<210> SEQ ID NO 1
<211> LENGTH: 146
<212> TYPE: PRT
<213> ORGANISM: Homo sapiens

<400> SEQUENCE: 1

Pro Ala Leu Pro Glu Asp Gly Gly Ser Gly Ala Phe Pro Pro Gly His
1               5                   10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
        35                  40                  45

Pro His Ile Lys Leu Gln Leu Gln Ala Glu Glu Arg Gly Val Val Ser
    50                  55                  60

Ile Lys Gly Val Cys Ala Asn Arg Tyr Leu Ala Met Lys Glu Asp Gly
65                  70                  75                  80

Arg Leu Leu Ala Ser Lys Cys Val Thr Asp Glu Cys Phe Phe Phe Glu
                85                  90                  95

Arg Leu Glu Ser Asn Asn Tyr Asn Thr Tyr Arg Ser Arg Lys Tyr Thr
            100                 105                 110

Ser Trp Tyr Val Ala Leu Lys Arg Thr Gly Gln Tyr Lys Leu Gly Ser
        115                 120                 125

Lys Thr Gly Pro Gly Gln Lys Ala Ile Leu Phe Leu Pro Met Ser Ala
    130                 135                 140

Lys Ser
145

<210> SEQ ID NO 2
<211> LENGTH: 146
<212> TYPE: PRT
<213> ORGANISM: Bos taurus

<400> SEQUENCE: 2

Pro Ala Leu Pro Glu Asp Gly Gly Ser Gly Ala Phe Pro Pro Gly His
1               5                   10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
        35                  40                  45

Pro His Ile Lys Leu Gln Leu Gln Ala Glu Glu Arg Gly Val Val Ser
    50                  55                  60

Ile Lys Gly Val Cys Ala Asn Arg Tyr Leu Ala Met Lys Glu Asp Gly
65                  70                  75                  80

Arg Leu Leu Ala Ser Lys Cys Val Thr Asp Glu Cys Phe Phe Phe Glu
                85                  90                  95
```

```
Arg Leu Glu Ser Asn Asn Tyr Asn Thr Tyr Arg Ser Arg Lys Tyr Ser
            100                 105                 110

Ser Trp Tyr Val Ala Leu Lys Arg Thr Gly Gln Tyr Lys Leu Gly Pro
        115                 120                 125

Lys Thr Gly Pro Gly Gln Lys Ala Ile Leu Phe Leu Pro Met Ser Ala
    130                 135                 140

Lys Ser
145

<210> SEQ ID NO 3
<211> LENGTH: 155
<212> TYPE: PRT
<213> ORGANISM: Homo sapiens

<400> SEQUENCE: 3

Met Ala Ala Gly Ser Ile Thr Thr Leu Pro Ala Leu Pro Glu Asp Gly
 1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 4
<211> LENGTH: 155
<212> TYPE: PRT
<213> ORGANISM: Bos taurus

<400> SEQUENCE: 4

Met Ala Ala Gly Ser Ile Thr Thr Leu Pro Ala Leu Pro Glu Asp Gly
 1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110
```

```
                Asn Thr Tyr Arg Ser Arg Lys Tyr Ser Ser Trp Tyr Val Ala Leu Lys
                                115                 120                 125

Arg Thr Gly Gln Tyr Lys Leu Gly Pro Lys Thr Gly Pro Gly Gln Lys
                130                 135                 140

Ala Ile Leu Phe Leu Pro Met Ser Ala Lys Ser
                145                 150                 155

<210> SEQ ID NO 5
<211> LENGTH: 441
<212> TYPE: DNA
<213> ORGANISM: Homo sapiens
<220> FEATURE:
<221> NAME/KEY: CDS
<222> LOCATION: (1)...(441)

<400> SEQUENCE: 5 ccc gcc ttg ccc gag gat ggc ggc agc ggc gcc ttc ccg ccc ggc cac        48
Pro Ala Leu Pro Glu Asp Gly Gly Ser Gly Ala Phe Pro Pro Gly His
1               5                   10                  15 ttc aag gac ccc aag cgg ctg tac tgc aaa aac ggg ggc ttc ttc ctg        96
Phe Lys Asp Pro Lys Arg Leu Tyr Cys Lys Asn Gly Gly Phe Phe Leu
                20                  25                  30 cgc atc cac ccc gac ggc cga gtt gac ggg gtc cgg gag aag agc gac      144
Arg Ile His Pro Asp Gly Arg Val Asp Gly Val Arg Glu Lys Ser Asp
            35                  40                  45 cct cac atc aag cta caa ctt caa gca gaa gag aga gga gtt gtg tct      192
Pro His Ile Lys Leu Gln Leu Gln Ala Glu Glu Arg Gly Val Val Ser
        50                  55                  60 atc aaa gga gtg tgt gct aac cgt tac ctg gct atg aag gaa gat gga      240
Ile Lys Gly Val Cys Ala Asn Arg Tyr Leu Ala Met Lys Glu Asp Gly
65                  70                  75                  80 aga tta ctg gct tct aaa tgt gtt acg gat gag tgt ttc ttt ttt gaa      288
Arg Leu Leu Ala Ser Lys Cys Val Thr Asp Glu Cys Phe Phe Phe Glu
                85                  90                  95 cga ttg gaa tct aat aac tac aat act tac cgg tca agg aaa tac acc      336
Arg Leu Glu Ser Asn Asn Tyr Asn Thr Tyr Arg Ser Arg Lys Tyr Thr
                100                 105                 110 agt tgg tat gtg gca ctg aaa cga act ggg cag tat aaa ctt gga tcc      384
Ser Trp Tyr Val Ala Leu Lys Arg Thr Gly Gln Tyr Lys Leu Gly Ser
            115                 120                 125 aaa aca gga cct ggg cag aaa gct ata ctt ttt ctt cca atg tct gct      432
Lys Thr Gly Pro Gly Gln Lys Ala Ile Leu Phe Leu Pro Met Ser Ala
        130                 135                 140 aag agc tga                                                          441
Lys Ser *
145

<210> SEQ ID NO 6
<211> LENGTH: 441
<212> TYPE: DNA
<213> ORGANISM: Bos taurus
<220> FEATURE:
<221> NAME/KEY: CDS
<222> LOCATION: (1)...(441)

<400> SEQUENCE: 6 cca gcc cta cca gaa gat ggg ggg tcc ggg gcc ttc cca ccc ggg cac        48
Pro Ala Leu Pro Glu Asp Gly Gly Ser Gly Ala Phe Pro Pro Gly His
1               5                   10                  15 ttc aaa gat cca aaa cga cta tat tgt aaa aac ggg ggg ttc ttc cta        96
Phe Lys Asp Pro Lys Arg Leu Tyr Cys Lys Asn Gly Gly Phe Phe Leu
                20                  25                  30 cga atc cac cca gat ggg cga gta gat ggg gta cga gaa aaa tcc gat      144
```

```
                        Arg Ile His Pro Asp Gly Arg Val Asp Gly Val Arg Glu Lys Ser Asp
                                 35                  40                  45 cca cac atc aaa cta caa cta caa gcc gaa gaa cga ggg gta gta tcc                192
Pro His Ile Lys Leu Gln Leu Gln Ala Glu Glu Arg Gly Val Val Ser
 50                  55                  60 atc aaa ggg gta tgt gcc aac cga tat cta gcc atg aaa gaa gat ggg                240
Ile Lys Gly Val Cys Ala Asn Arg Tyr Leu Ala Met Lys Glu Asp Gly
 65                  70                  75                  80 cga cta cta gcc tcc aaa tgt gta acc gat gaa tgt ttc ttc ttc gaa                288
Arg Leu Leu Ala Ser Lys Cys Val Thr Asp Glu Cys Phe Phe Phe Glu
                 85                  90                  95 cga cta gaa tcc aac aac tat aac acc tat cga tcc cga aaa tat tcc                336
Arg Leu Glu Ser Asn Asn Tyr Asn Thr Tyr Arg Ser Arg Lys Tyr Ser
            100                 105                 110 tcc tgg tat gta gcc cta aaa cga acc ggg caa tat aaa cta ggg cca                384
Ser Trp Tyr Val Ala Leu Lys Arg Thr Gly Gln Tyr Lys Leu Gly Pro
        115                 120                 125 aaa acc ggg cca ggg caa aaa gcc atc cta ttc cta cca atg tcc gcc                432
Lys Thr Gly Pro Gly Gln Lys Ala Ile Leu Phe Leu Pro Met Ser Ala
130                 135                 140 aaa tcc taa                                                                    441
Lys Ser *
145

<210> SEQ ID NO 7
<211> LENGTH: 468
<212> TYPE: DNA
<213> ORGANISM: Homo sapiens
<220> FEATURE:
<221> NAME/KEY: CDS
<222> LOCATION: (1)...(468)

<400> SEQUENCE: 7 atg gca gcc ggg agc atc acc acg ctg ccc gcc ttg ccc gag gat ggc                 48
Met Ala Ala Gly Ser Ile Thr Thr Leu Pro Ala Leu Pro Glu Asp Gly
 1               5                  10                  15 ggc agc ggc gcc ttc ccg ccc ggc cac ttc aag gac ccc aag cgg ctg                 96
Gly Ser Gly Ala Phe Pro Pro Gly His Phe Lys Asp Pro Lys Arg Leu
             20                  25                  30 tac tgc aaa aac ggg ggc ttc ttc ctg cgc atc cac ccc gac ggc cga                144
Tyr Cys Lys Asn Gly Gly Phe Phe Leu Arg Ile His Pro Asp Gly Arg
         35                  40                  45 gtt gac ggg gtc cgg gag aag agc gac cct cac atc aag cta caa ctt                192
Val Asp Gly Val Arg Glu Lys Ser Asp Pro His Ile Lys Leu Gln Leu
 50                  55                  60 caa gca gaa gag aga gga gtt gtg tct atc aaa gga gtg tgt gct aac                240
Gln Ala Glu Glu Arg Gly Val Val Ser Ile Lys Gly Val Cys Ala Asn
 65                  70                  75                  80 cgt tac ctg gct atg aag gaa gat gga aga tta ctg gct tct aaa tgt                288
Arg Tyr Leu Ala Met Lys Glu Asp Gly Arg Leu Leu Ala Ser Lys Cys
                 85                  90                  95 gtt acg gat gag tgt ttc ttt ttt gaa cga ttg gaa tct aat aac tac                336
Val Thr Asp Glu Cys Phe Phe Phe Glu Arg Leu Glu Ser Asn Asn Tyr
            100                 105                 110 aat act tac cgg tca agg aaa tac acc agt tgg tat gtg gca ctg aaa                384
Asn Thr Tyr Arg Ser Arg Lys Tyr Thr Ser Trp Tyr Val Ala Leu Lys
        115                 120                 125 cga act ggg cag tat aaa ctt gga tcc aaa aca gga cct ggg cag aaa                432
Arg Thr Gly Gln Tyr Lys Leu Gly Ser Lys Thr Gly Pro Gly Gln Lys
130                 135                 140 gct ata ctt ttt ctt cca atg tct gct aag agc tga                                468
Ala Ile Leu Phe Leu Pro Met Ser Ala Lys Ser *
145                 150
```

<210> SEQ ID NO 8
<211> LENGTH: 468
<212> TYPE: DNA
<213> ORGANISM: Bos taurus
<220> FEATURE:
<221> NAME/KEY: CDS
<222> LOCATION: (1)...(468)

<400> SEQUENCE: 8

| | | | | | | | | | | | | | | | | |
|---|---|---|---|---|---|---|---|---|---|---|---|---|---|---|---|---|
| atg | gca | gcc | ggg | agc | atc | acc | acg | ctg | cca | gcc | cta | cca | gaa | gat | ggg | 48 |
| Met | Ala | Ala | Gly | Ser | Ile | Thr | Thr | Leu | Pro | Ala | Leu | Pro | Glu | Asp | Gly | |
| 1 | | | | 5 | | | | | 10 | | | | | 15 | | |
| ggg | tcc | ggg | gcc | ttc | cca | cca | ggg | cac | ttc | aaa | gat | cca | aaa | cga | cta | 96 |
| Gly | Ser | Gly | Ala | Phe | Pro | Pro | Gly | His | Phe | Lys | Asp | Pro | Lys | Arg | Leu | |
| | | | 20 | | | | | 25 | | | | | 30 | | | |
| tat | tgt | aaa | aac | ggg | ggg | ttc | ttc | cta | cga | atc | cac | cca | gat | ggg | cga | 144 |
| Tyr | Cys | Lys | Asn | Gly | Gly | Phe | Phe | Leu | Arg | Ile | His | Pro | Asp | Gly | Arg | |
| | | 35 | | | | | 40 | | | | | 45 | | | | |
| gta | gat | ggg | gta | cga | gaa | aaa | tcc | gat | cca | cac | atc | aaa | cta | caa | cta | 192 |
| Val | Asp | Gly | Val | Arg | Glu | Lys | Ser | Asp | Pro | His | Ile | Lys | Leu | Gln | Leu | |
| 50 | | | | | 55 | | | | | 60 | | | | | | |
| caa | gcc | gaa | gaa | cga | ggg | gta | gta | tcc | atc | aaa | ggg | gta | tgt | gcc | aac | 240 |
| Gln | Ala | Glu | Glu | Arg | Gly | Val | Val | Ser | Ile | Lys | Gly | Val | Cys | Ala | Asn | |
| 65 | | | | | 70 | | | | | 75 | | | | | 80 | |
| cga | tat | cta | gcc | atg | aaa | gaa | gat | ggg | cga | cta | cta | gcc | tcc | aaa | tgt | 288 |
| Arg | Tyr | Leu | Ala | Met | Lys | Glu | Asp | Gly | Arg | Leu | Leu | Ala | Ser | Lys | Cys | |
| | | | | 85 | | | | | 90 | | | | | 95 | | |
| gta | acc | gat | gaa | tgt | ttc | ttc | ttc | gaa | cga | cta | gaa | tcc | aac | aac | tat | 336 |
| Val | Thr | Asp | Glu | Cys | Phe | Phe | Phe | Glu | Arg | Leu | Glu | Ser | Asn | Asn | Tyr | |
| | | | 100 | | | | | 105 | | | | | 110 | | | |
| aac | acc | tat | cga | tcc | cga | aaa | tat | tcc | tcc | tgg | tat | gta | gcc | cta | aaa | 384 |
| Asn | Thr | Tyr | Arg | Ser | Arg | Lys | Tyr | Ser | Ser | Trp | Tyr | Val | Ala | Leu | Lys | |
| | | 115 | | | | | 120 | | | | | 125 | | | | |
| cga | acc | ggg | caa | tat | aaa | cta | ggg | cca | aaa | acc | ggg | cca | ggg | caa | aaa | 432 |
| Arg | Thr | Gly | Gln | Tyr | Lys | Leu | Gly | Pro | Lys | Thr | Gly | Pro | Gly | Gln | Lys | |
| 130 | | | | | 135 | | | | | 140 | | | | | | |
| gcc | atc | cta | ttc | cta | cca | atg | tcc | gcc | aaa | tcc | taa | | | | | 468 |
| Ala | Ile | Leu | Phe | Leu | Pro | Met | Ser | Ala | Lys | Ser | * | | | | | |
| 145 | | | | 150 | | | | | 155 | | | | | | | |

STABILIZED FGF FORMULATIONS CONTAINING REDUCING AGENTS

CROSS-REFERENCE TO RELATED APPLICATION

This application claims the benefit of U.S. Provisional Application Ser. No. 60/229,238, filed Aug. 31, 2000, entitled "Stabilized FGF Formulations Containing Reducing Agents," the content of which is herein incorporated by reference in its entirety.

FIELD OF THE INVENTION

The invention relates generally to pharmaceutical compositions, more particularly to stabilized liquid or lyophilized formulations comprising fibroblast growth factor (FGF) or variant thereof.

BACKGROUND OF THE INVENTION

Advances in recombinant DNA technology have provided a wide variety of tools for protein production and purification in sufficiently large quantities for use as drugs. However, proteins are prone to undergo physical or chemical changes in liquid or even lyophilized formulations, including denaturation, formation of soluble and insoluble aggregates, hydrolysis, or oxidation. These changes often lead to the loss or reduction of the pharmaceutical activity of the protein of interest. To date, the stabilization and preservation of recombinant proteins in liquid or lyophilized formulations remain a challenge.

The fibroblast growth factors (FGFs) are a family of growth factors that bind to proteoglycans. These growth factors are potent mitogens that are essential to the growth and differentiation of the cells involved in wound healing. Fibroblast growth factor 2 (FGF-2) is a heparin-binding growth factor that belongs to this family. FGF-2 has pleiotropic roles in multiple tissue and cell types, including its mitogenic, angiogenic, and survival factor activities. FGF-2 is involved in cell migration, cell differentiation, and in a variety of developmental processes. Its therapeutic potential has been examined in clinical trials involving wound healing and treatment of ischemic cardiovascular diseases.

Although early pharmaceutical preparations of FGF-2 were shown to be biologically active through in vitro cell assays, these formulations produced heterogeneous mixtures after short-term storage at room temperature, under refrigeration, or in the frozen state. In addition, insoluble aggregates can form in aged solution formulations at higher FGF-2 concentrations (1 mg/ml or greater) and in lyophilized formulations. Methods for preparing stabilized FGF-2 formulations have been under pursuit. See, for example, U.S. Pat. Nos. 5,217,954, 5,202,311, 5,130,418; and PCT Publication WO 92/01442. As oxidation is one of the major destructive processes contributing to FGF-2 instability, formulations that reduce FGF-2 oxidation are needed.

SUMMARY OF THE INVENTION

Compositions comprising fibroblast growth factor (FGF) as a therapeutically active component and methods useful in their preparation are provided. The compositions are stabilized liquid or lyophilized pharmaceutical formulations comprising fibroblast growth factor and a reducing agent, where the reducing agent is present in an amount sufficient to inhibit oxidation of fibroblast growth factor. The reducing agent is effective in those FGF compositions and formulations lacking in disulfide bonds wherein only free sulfhydryl groups are present. The compositions further comprise a buffering agent to maintain pH of the liquid composition within an acceptable range for stability of the FGF polypeptide.

The reducing agent is a thiol derivative, which serves to protect the FGF polypeptide against oxidation during storage of the liquid or lyophilized formulation. Such liquid or lyophilized formulations are said to be stabilized, as addition of the reducing agent results in these compositions having increased storage stability relative to liquid or lyophilized compositions formulated in the absence of the reducing agent.

Methods for increasing stability of FGF in a liquid or lyophilized formulation and for increasing storage stability of such a formulation are also provided. The methods comprise incorporating into the liquid or lyophilized FGF formulation an amount of a reducing agent sufficient to decrease oxidation of FGF during storage of the formulation. The methods find use in preparation of the liquid or lyophilized FGF compositions of the invention.

DETAILED DESCRIPTION OF THE INVENTION

Figure 1:
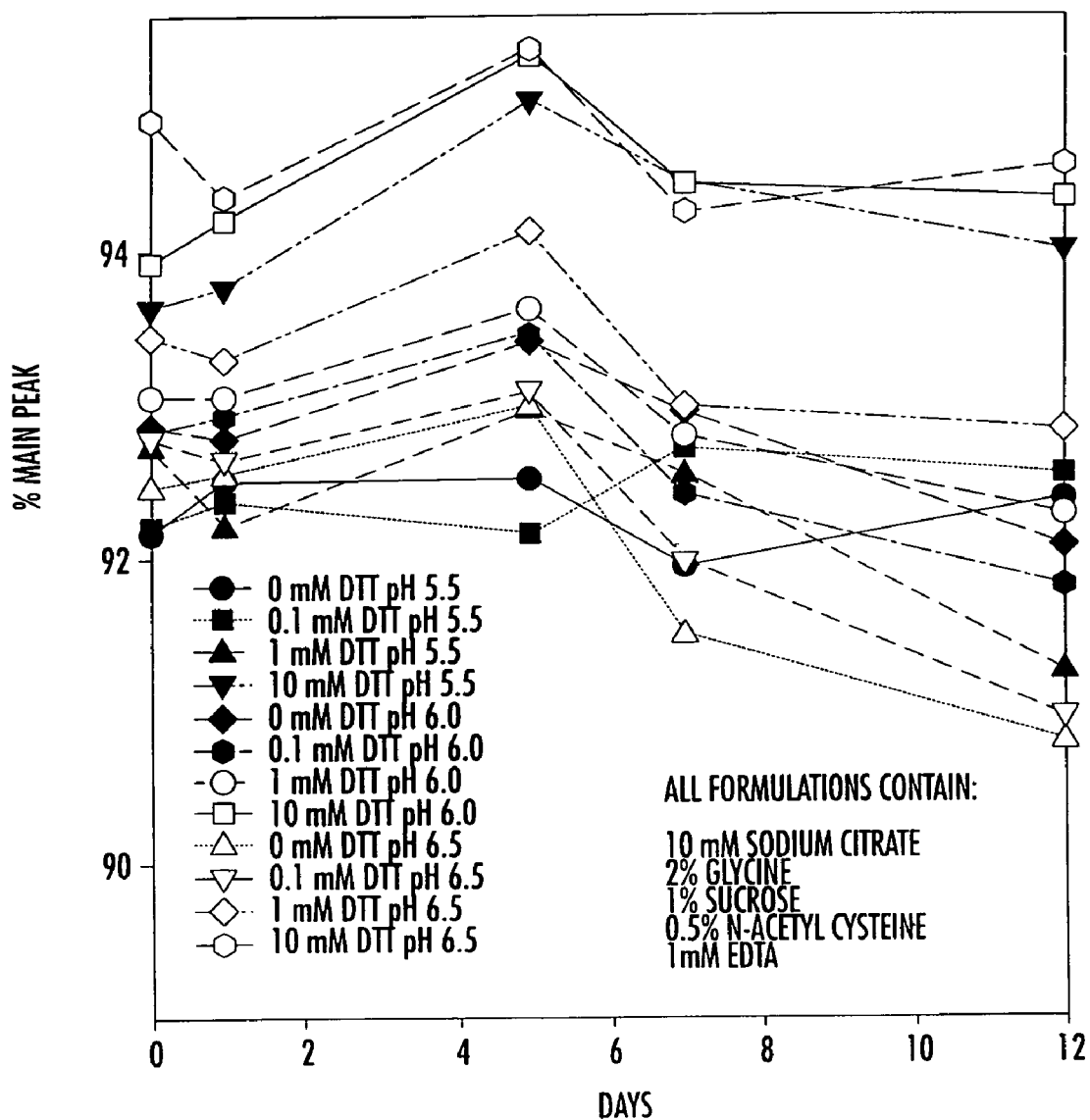
FIG. 1 shows the percentage of the main peak remaining during storage of the different liquid FGF-2 formulations at 4° C. The formulations contain 10 mM sodium citrate, 2% glycine, 1% sucrose, 0.5% n-acetyl cysteine, 1 mM EDTA, and DTT in a concentration of 0 mM, 0.1 mM, 1 mM, or 10 mM. Each formulation was tested for stability at pH 5.5, 6.0, and 6.5.

The present invention is directed to stabilized liquid or lyophilized fibroblast growth factor pharmaceutical formulations and methods useful in their preparation. For purposes of the present invention, the term "liquid" with regard to growth factor pharmaceutical formulations is intended to include the term "aqueous." The term "lyophilize" with regard to growth factor pharmaceutical formulations is intended to refer to rapid freeze drying under reduced pressure of a plurality of vials, each containing a unit dose of the fibroblast growth factor formulation of the present invention therein. Lyophilizers, which perform the above described lyophilization, are commercially available and readily operable by those skilled in the art.

The stabilized pharmaceutical formulations of the invention comprise fibroblast growth factors and variants thereof. The fibroblast growth factors (FGF) are a family of at least twenty-three structurally related polypeptides (named FGF-1 to FGF-23) that are characterized by a high degree of affinity for proteoglycans, such as heparin. The various FGF molecules range in size from 15 to at least 32.5 kDa, and exhibit a broad range of biological activities in normal and malignant conditions including nerve cell adhesion and differentiation (Schubert et al. (1987) *J. Cell Biol.* 104:635-643); wound healing (U.S. Pat. No. 5,439,818 (Fiddes)); as mitogens toward many mesodermal and ectodermal cell types, as trophic factors, as differentiation inducing or inhibiting factors (Clements et al. (1993) *Oncogene* 8:1311-1316); and as an angiogenic factor (Harada (1994) *J. Clin. Invest.* 94:623-630). Thus, the FGF family is a family of pluripotent growth factors that stimulate to varying extents fibroblasts, smooth muscle cells, epithelial cells, endothelial cells, myocytes, and neuronal cells. Preferably the FGF is FGF-2 (also known as basic FGF), FGF-4, FGF-5, FGF-18, more preferably FGF-2, or variant thereof as described elsewhere herein.

Fibroblast growth factors, more particularly FGFs with free sulfhydryl groups, e.g., FGF-2, are susceptible to oxidation and aggregate formation during storage. Both of these processes impair biological activity of these proteins, and hence decrease therapeutic efficacy of FGF-containing pharmaceutical formulations. FGF formulations made in accordance with the methods of the present invention provide for greater retention of this protein in its reduced state, and hence increased storage stability.

The stabilized FGF pharmaceutical formulations further comprise at least one reducing agent in an amount sufficient to inhibit oxidation of FGF. By "an amount sufficient to inhibit oxidation" is intended an amount that reduces accumulation of oxidized FGF species during storage relative to FGF formulations prepared without the said reducing agent. Inhibiting FGF oxidation, particularly as occurs with the surface-exposed cysteine residues on FGF, results in greater retention of FGF in its properly reduced, biologically active form. As a result of reduced oxidation with time, the FGF formulations of the invention have increased storage stability relative to a liquid or lyophilized FGF formulation prepared without the reducing agent. The reducing agent is selected from the family of compounds known as thiol derivatives. Thiol derivatives for use in the stabilized FGF formulations of the invention include, but are not limited to, dithiothreitol (DTT), n-acetyl-cysteine, thioglycolic acid, thiolactic acid, glutathione, or a combination thereof. In a preferred embodiment, the reducing agent is dithiothreitol.

The effect of a particular reducing agent on FGF oxidation, and hence its stability over time within a pharmaceutical formulation, can readily be determined by measuring the change in the oxidative state of this protein within the formulation. The amount of FGF that remains in the reduced state can be quantified by a number of analytical assays adapted to detect FGF. Such assays include, for example, size-exclusion (SEC)-HPLC, UV absorbance, and reverse phase (RP)-HPLC as described in the Examples below. Thus, for example, where RP-HPLC is used to monitor stability of FGF in a liquid or lyophilized formulation, the effect of a particular reducing agent on oxidation would be reflected in the size of the percent main peak for the RP-HPLC profile. Oxidation of FGF is detected as a decrease in the percent main peak. Stability of FGF in the presence of differing concentrations of a particular reducing agent can thus be measured by monitoring the change in the percent main peak over time.

Determination of the amount of a particular reducing agent to be added to a liquid or lyophilized FGF pharmaceutical formulation to inhibit oxidation and increase retention of FGF in its reduced state, thereby increasing FGF stability and thus increasing storage stability of the formulation, can readily be determined without undue experimentation using methods generally known to one of skill in the art. Thus, for example, the preferred amount of reducing agent to be added can be determined empirically by preparing the liquid or lyophilized formulation comprising FGF with different concentrations of the reducing agent, or combination of reducing agents, and determining the relative effect on formation of oxidative species of FGF using, for instance, chromatographic separation of the molecular species, such as with RP-HPLC. Following the protocols disclosed, for example, in Example 1 below, the skilled artisan may assess a range of desired concentrations of the reducing agent for use in the liquid or lyophilized compositions described herein. Preferably the amount of reducing agent incorporated into the composition is within a concentration range of about 0.01 mM to about 50 mM, preferably about 0.05 mM to about 30 mM, more preferably about 0.1 mM to about 25 mM, even more preferably about 0.25 mM to about 20 mM, still more preferably about 0.5 mM to about 15 mM, even more preferably about 1 mM to about 12 mM. When the reducing agent is DTT, the preferred concentration of the reducing agent is about 10 mM. The amount of reducing agent in the formulation can also be calculated by the percentage of dry weight of the reducing agent in the volume of solution. Preferably the amount of reducing agent incorporated into the composition is within a concentration range of about 0.1% to about 5%, more preferably about 0.2% to about 2%, even more preferably about 0.4% to about 1%. For example, for formulations containing n-acetyl-cysteine as the reducing agent, the preferred concentration of n-acetyl-cysteine is about 0.5%.

The liquid or lyophilized FGF pharmaceutical formulations of the present invention are "stabilized" compositions. By "stabilized" is intended the FGF formulations have increased storage stability relative to FGF formulations prepared in the absence of a reducing agent or combination thereof as disclosed herein. This increased storage stability is observed in the liquid formulation, when stored as a liquid within the range of about 2° C. to about 40° C., more preferably at refrigerated temperatures, e.g., about 2° C. to about 8° C., and most preferably about 4° C. When prepared in a dried form, such as a lyophilized, air-dried, or spray-dried form, it can be stored at room temperature and reconstituted into a liquid form for immediate use or for storage at refrigerated temperatures for future use. An amount of reducing agent sufficient to stabilize FGF in a liquid or lyophilized formulation would be viewed as an amount that resulted in decreased oxidation of FGF over time, and hence greater retention of FGF in the formulation in its reduced, biologically active form. Such an effect would be detected, for example, as greater retention of the main peak in the RP-HPLC assay.

In combination with the reducing agent as defined herein, the stabilized liquid or lyophilized FGF-2 formulation of the invention further comprises a buffer to maintain pH of the composition. The buffering agent may be any buffer solution that provides a pH that promotes stability of FGF. The buffer used to achieve the pH of the FGF formulation can be any acceptable buffer capable of maintaining the pH in the desired range upon addition of acid or alkali and which is not biologically or otherwise undesirable, i.e., the buffer does not cause undesirable biological effects and does not interact in a deleterious manner with any of the other components of the composition. For example, where the composition will be administered to a human, the buffer should be nontoxic to humans (at least nontoxic at the dosages used). Suitable buffers include, but are not limited to, phosphoric acid buffers, carbonic acid buffers, including for example, glutaric acid, maleic acid, succinic acid, citric acid, imidazole, or histidine, in concentrations suitable to achieve the desired pH, e.g., in the range of 0.5 to 50 mM, preferably about 1 mM to about 40 mM, more preferably about 2 mM to about 30 mM, even more preferably about 5 mM to about 20 mM, more preferably about 8 mM to about 15 mM, most preferably, about 10 mM. If the stabilized liquid FGF formulation of the invention is lyophilized prior to use, reconstitution of the composition can be achieved using a buffer as described above, so that the composition is of the desired pH. Additionally, the buffer components can also be freeze-dried or concentrated and upon reconstitution, provide the desired pH for the composition.

In addition to the maintenance of an acceptable and desirable pH, where the FGF formulation is used for delivery to a mammal such as a human, the isotonicity of the composition is also a consideration. Thus, the preferred composition for an injectable solution of FGF will provide an isotonicity the same as, or similar to, that of patient serum or body fluids. To achieve the isotonicity, a salt such as sodium chloride, potassium chloride, a phosphate buffer, dextrose, or sucrose, can be added to the solution, at an appropriate concentration. For example, if sodium chloride is used, about a 150 mM sodium chloride solution will provide adequate isotonicity. Also, sugars such as glucose at about 9% can be utilized in the composition.

As shown in the examples below, pH of a liquid or lyophilized formulation affects the stability of FGF contained therein, primarily through its affect on FGF oxidation. Thus the amount of buffering agent present in the compositions of the invention will vary depending upon the pH optimum for stability of a particular fibroblast growth factor of interest. Determination of this pH optimum can be achieved using methods generally available in the art, and further illustrated in the Examples described herein. The preferred pH range could encompass formulations of about pH 3.0-7.5. Suitable pH's include about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5. Suitable pH ranges are about 4.5-7.2; about 4.6-7.1; about 4.7-7.0; about 4.8-6.9 about 4.9-6.8, about 5.0-6.7; about 5.1-6.6; about 5.2-6.5; about 5.3-6.4; about 5.4-6.3; about 5.5-6.2; about 5.7-6.1; and about 5.8-6.0. A preferred range is about pH 5.0-6.5. Most preferably, the pH is about 6.0. For compositions containing FGF-2 and DTT, the preferred pH is about 6.0. For compositions containing FGF-2 and n-acetylcysteine as the sole reducing agent, the preferred pH is about 5.5.

The stabilized FGF liquid or lyophilized formulations comprising a reducing agent and suitable buffer may also comprise additional agents that further enhance stability of FGF. Stabilizing agents of particular interest to the present invention include, but are not limited to, glycine, which is also used to adjust the isotonicity of the formulation to the desired level. The range of glycine concentration is about 0.5% to about 5%, preferably about 2% to about 4%. Thus, in one embodiment, the preferred glycine concentration is about 2%, 3%, or 4%.

In addition, other stabilizing agents, such as ethylenediaminetetraacetic acid (EDTA) or one of its salts such as disodium EDTA, can be added to further enhance the stability of the liquid or lyophilized compositions. The EDTA acts as a scavenger of metal ions known to catalyze many oxidation reactions, thus providing an additional stabilizing agent. Preferably, the concentration of EDTA is between about 0.1 mM to about 5 mM, more preferably about 1 mM.

Where desirable, sugars or sugar alcohols may also be included in the stabilized liquid or lyophilized FGF formulations of the present invention. Any sugar such as mono-, di-, or polysaccharides, or water-soluble glucans, including for example fructose, glucose, mannose, sorbose, xylose, maltose, lactose, sucrose, dextran, trehalose, pullulan, dextrin, cyclodextrin, soluble starch, hydroxyethyl starch, and carboxymethylcellulose-Na may be used. Sucrose is the most preferred sugar additive. Sugar alcohol is defined as a C4-C8 hydrocarbon having a —OH group and includes, for example, mannitol, sorbitol, inositol, galactitol, dulcitol, xylitol, and arabitol with mannitol being the most preferred sugar alcohol additive. The sugars or sugar alcohols mentioned above may be used individually or in combination. There is no fixed limit to the amount used, as long as the sugar or sugar alcohol is soluble in the liquid preparation and does not adversely affect the stabilizing effects achieved using the methods of the invention. Preferably, the sugar or sugar alcohol concentration is between 0.1% to 5.0%, or preferably between about 1.0 and about 10.0 w/v %, more preferably between about 2.0 and about 6.0 w/v %.

Thus, in one embodiment, the stabilized FGF liquid formulation comprises sodium citrate at a concentration of about 1 mM to about 50 mM, glycine at a concentration of about 1% to about 5%, sucrose at a concentration of about 0.1% to about 5%, acetyl cysteine at a concentration of about 0.1% to about 5%, EDTA at a concentration of about 0.1 mM to about 5 mM, and DTT at a concentration of about 0.1 mM to about 10 mM, with a pH of about 5.0 to about 6.5. More preferably, the stabilized FGF liquid formulation comprises 10 mM sodium citrate, 2% glycine, 1% sucrose, 0.5% n-acetyl cysteine, 1 mM EDTA, and 10 mM DTT, at pH 5.5.

The stabilized liquid pharmaceutical compositions of the invention may contain other compounds that increase the effectiveness or promote the desirable qualities of the FGF of interest so long as the primary stabilizing effect achieved with the reducing agent is not adversely affected. The composition must be safe for administration via the route that is chosen, it must be sterile, and must retain its desired therapeutic activity. Having identified the advantages of preparing FGF formulations with a reducing agent as described herein, it is within skill in the art to determine, without undue experimentation, preferred concentrations of each of these additional components to be incorporated into a liquid or lyophilized FGF pharmaceutical composition to achieve increased FGF stability beyond that obtained with addition of the reducing agent.

Compositions of the present invention are preferably prepared by premixing the stabilizing and buffering agents, and any other excipients prior to incorporation of the FGF of interest. Any additional excipients that may be added to further stabilize the compositions of the present invention must not adversely affect the stabilizing effects of the primary stabilizing agent, i.e., a reducing agent, when used in combination with the buffering agent, to obtain the novel compositions disclosed herein. Following addition of a preferred amount of reducing agent to achieve decreased oxidation of an FGF of interest, pH of the liquid composition is adjusted using the buffering agent, preferably within a range disclosed herein, more preferably to the pH optimum for the FGF of interest. Although pH can be adjusted following addition of the FGF of interest into the composition, preferably it is adjusted prior to addition of FGF, as this can reduce the risk of denaturation of FGF. Appropriate mechanical devices are then used for achieving a proper mix of constituents.

While specific embodiments of the invention are directed to stabilized compositions comprising FGF-2 or variants thereof, which are particularly susceptible to oxidation, the utility of the invention extends generally to any FGF or variant thereof that exhibits oxidation during storage in a liquid or lyophilized formulation.

The FGF present in the stabilized liquid or lyophilized formulation of the invention may be native or obtained by recombinant techniques, and may be from any source, including mammalian sources such as, e.g., avian, mouse, rat, rabbit, primate, porcine, canine, bovine, equine, and human, provided they meet the criterion specified herein, that is, provided they become oxidized during storage in liquid or lyophilized formulations. Generally, the FGF is from a mammalian species such as bovine or human. Preferably such FGFs are derived from a human source, and more preferably are recombinant, human proteins from microbial hosts.

Biologically active variants of an FGF of interest that serves as a therapeutically active component in the stabilized liquid or lyophilized formulation of the invention are also encompassed by the term "FGF" as used herein. Such variants should retain the desired biological activity of the native FGF such that the liquid or lyophilized formulation comprising the variant FGF has the same therapeutic effect as the liquid or lyophilized formulation comprising the native FGF when administered to a subject. That is, the variant FGF will serve as a therapeutically active component in the liquid or lyophilized formulation in a manner similar to that observed for the native FGF. Methods are available in the art for determining whether a variant FGF retains the desired biological activity, and hence serves as a therapeutically active component in the liquid or lyophilized formulation. Biological activity can be measured using assays specifically designed for measuring activity of the native FGF, including assays measuring fibroblast growth promoting activity, growth stimulating activity of capillary endothelial cells, and angiogenic activity. See U.S. Pat. No. 5,852,177, herein incorporated by reference.

Thus, for example, the variants may be measured for angiogenic activity using representative assays, including known radioreceptor assays using placental membranes (see, e.g., U.S. Pat. No. 5,324,639; Hall et al. (1974) *J. Clin. Endocrinol. and Metab.* 39:973-976; and Marshall et al. (1974) *J. Clin. Endocrinol. and Metab.* 39:283-292). Additional assays include mitogenic activity as determined in an in vitro assay of endothelial cell proliferation. This activity is preferably determined in a human umbilical vein endothelial (HUVE) cell-based assay, as described, for example, in any of the following publications: Gospodarowicz et al. (1989) *Proc. Natl. Acad. Sci. USA* 87:7311-7315; Ferrara and Henzel (1989) *Biochem. Biophys. Res. Commun.* 161:851-858; Conn et al. (1990) *Proc. Natl. Acad. Sci. USA* 87:1323-1327; Soker et al. (1998) *Cell* 92:735-745; Waltenberger et al. (1994) *J. Biol. Chem.* 269:26988-26995; Siemmeister et al. (1996) *Biochem. Biophys. Res. Commun.* 222:249-255; Fiebich et al. (1993) *Eur. J. Biochem.* 211:19-26; Cohen et al. (1993) *Growth Factors* 7:131-138. A further biological activity is involvement in angiogenesis and/or vascular remodeling, which can be tested, for example, in the corneal pocket angiogenesis assay as described in Connolly et al. (1989) *J. Clin. Invest.* 84:1470-1478 and Lobb et al. (1985) *Biochemistry* 24:4969-4973; the endothelial cell tube formation assay, as described for example in Pepper et al. (1992) *Biochem. Biophys. Res. Commun.* 189:824-831; Goto et al. (1993) *Lab. Invest.* 69:508-517; or Koolwijk et al. (1996) *Cell Biol.* 132: 1177-1188; the chick chorioallantoic membrane (CAM) angiogenesis assay as described for example in Pluet et al. (1989) *EMBO. J.* 8:3801-3806; the endothelial cell mitogenesis assay as described in Bohlen et al. (1984) *Proc. Natl. Acad. Sci. USA* 81:5364-5368; Presta et al. (1986) *Mol. Gen. Biol.* 6:4060-4066; Klagsbrun and Shing (1985) *Proc. Natl. Acad. Sci. USA* 82:805-809; Gosodarowicz et al. (1985) *J. Cell. Physiol.* 122:323-332; or the endothelial cell migration assay as described in Moscatelli et al. (1986) *Proc. Natl. Acad. Sci. USA* 83:2091-2095; and Presta et al. (1986) *Mol. and Cell. Biol.* 6:4060-4066; all of which are herein incorporated by reference. Additionally, antibodies raised against a biologically active native FGF can be tested for their ability to bind to the variant FGF, where effective binding is indicative of an FGF having a conformation similar to that of the native FGF. It is recognized that one or more of the assays may be used. Preferably, the variant has at least the same activity as the native molecule.

Suitable biologically active variants of a native or naturally occurring FGF of interest can be fragments, analogues, or derivatives of that FGF. By "fragment" is intended a polypeptide consisting of only a part of the intact polypeptide sequence and structure, and can be a C-terminal deletion or N-terminal deletion of the native polypeptide. By "analogue" is intended an analogue of either the native FGF or of a fragment of the native FGF, where the analogue comprises a native FGF sequence and structure having one or more amino acid substitutions, insertions, or deletions. "Muteins," such as those described herein, and peptides having one or more peptoids (peptide mimics) are also encompassed by the term analogue (See International Publication No. WO 91/04282). By "derivative" is intended any suitable modification of the native polypeptide of interest, of a fragment of the native polypeptide, or of their respective analogues, such as glycosylation, phosphorylation, or other addition of foreign moieties, so long as the desired biological activity of the native FGF is retained. Methods for making FGF fragments, analogues, and derivatives are generally available in the art.

For example, amino acid sequence variants of the FGF polypeptide can be prepared by mutations in the cloned DNA sequence encoding the native polypeptide of interest. Methods for mutagenesis and nucleotide sequence alterations are well known in the art. See, for example, Walker and Gaastra, eds. (1983) *Techniques in Molecular Biology* (MacMillan Publishing Company, New York); Kundel (1985) *Proc. Natl. Acad. Sci. USA* 82:488-492; Kunkel et al. (1987) *Methods Enzymol.* 154:367-382; Sambrook et al. (1989) *Molecular Cloning: A Laboratory Manual* (2$^{nd}$ ed.; Cold Spring Harbor Laboratory Press, Plainview, N.Y.); U.S. Pat. No. 4,873,192; and the references cited therein; herein incorporated by reference. Guidance as to appropriate amino acid substitutions that do not affect biological activity of the FGF of interest may be found in the model of Dayhoff et al. (1978) in *Atlas of Protein Sequence and Structure* (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly⇔Ala, Val⇔Ile⇔Leu, Asp⇔Glu, Lys⇔Arg, Asn⇔Gln, and Phe⇔Trp⇔Tyr.

In constructing variants of the FGF of interest, modifications are made such that variants continue to possess the desired activity. Obviously, any mutations made in the DNA encoding the variant FGF must not place the sequence out of reading frame and preferably will not create complementary regions that could produce secondary mRNA structure.

Biologically active variants of an FGF of interest will generally have at least 70%, 75%, preferably at least 80%, 85%, more preferably about 90%, 91%, 92%, 93%, 94%, 95% or more, and most preferably about 96%, 97%, 98%, 99% or more amino acid sequence identity to the amino acid sequence of the reference FGF molecule, which serves as the basis for comparison. A biologically active variant of a native FGF of interest may differ from the native FGF by as few as 1-15 amino acids, as few as 1-10, such as 6-10, as few as 5, as few as 4, 3, 2, or even 1 amino acid residue. By "sequence identity" is intended the same amino acid residues are found within the variant polypeptide and the polypeptide molecule that serves as a reference when a specified, contiguous segment of the amino acid sequence of the variant is aligned and compared to the amino acid sequence of the reference molecule. The percentage sequence identity between two amino acid sequences is calculated by determining the number of positions at which the identical amino acid residue occurs in both sequences to yield the number of matched positions, dividing the number of matched positions by the total number of positions in the segment undergoing comparison to the reference molecule, and multiplying the result by 100 to yield the percentage of sequence identity.

For purposes of optimal alignment of the two sequences, the contiguous segment of the amino acid sequence of the variant may have additional amino acid residues or deleted amino acid residues with respect to the amino acid sequence of the reference molecule. The contiguous segment used for comparison to the reference amino acid sequence will comprise at least twenty (20) contiguous amino acid residues, and may be 30, 40, 50, 100, or more residues. Corrections for increased sequence identity associated with inclusion of gaps in the variant's amino acid sequence can be made by assigning gap penalties. Methods of sequence alignment are well known in the art for both amino acid sequences and for the nucleotide sequences encoding amino acid sequences.

Thus, the determination of percent identity between any two sequences can be accomplished using a mathematical algorithm. One preferred, non-limiting example of a mathematical algorithm utilized for the comparison of sequences is the algorithm of Myers and Miller (1988) *CABIOS* 4:11-17. Such an algorithm is utilized in the ALIGN program (version 2.0), which is part of the GCG sequence alignment software package. A PAM120 weight residue table, a gap length penalty of 12, and a gap penalty of 4 can be used with the ALIGN program when comparing amino acid sequences. Another preferred, nonlimiting example of a mathematical algorithm for use in comparing two sequences is the algorithm of Karlin and Altschul (1990) *Proc. Natl. Acad. Sci. USA* 87:2264, modified as in Karlin and Altschul (1993) Proc. Natl. Acad. Sci. USA 90:5873-5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to a nucleotide sequence encoding the polypeptide of interest. BLAST protein searches can be performed with the XBLAST program, score=50, wordlength=3, to obtain amino acid sequences homologous to the polypeptide of interest. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs can be used. See on the World Wide Web at ncbi.nlm.gov. Also see the ALIGN program (Dayhoff (1978) in *Atlas of Protein Sequence and Structure* 5:Suppl. 3 (National Biomedical Research Foundation, Washington, D.C.) and programs in the Wisconsin Sequence Analysis Package, Version 8 (available from Genetics Computer Group, Madison, Wis.), for example, the GAP program, where default parameters of the programs are utilized.

When considering percentage of amino acid sequence identity, some amino acid residue positions may differ as a result of conservative amino acid substitutions, which do not affect properties of protein function. In these instances, percent sequence identity may be adjusted upwards to account for the similarity in conservatively substituted amino acids. Such adjustments are well known in the art. See, for example, Myers and Miller (1988) *Computer Applic. Biol. Sci.* 4:11-17.

The precise chemical structure of an FGF depends on a number of factors. As ionizable amino and carboxyl groups are present in the molecule, a particular polypeptide may be obtained as an acidic or basic salt, or in neutral form. All such preparations that retain their biological activity when placed in suitable environmental conditions are included in the definition of FGFs as used herein. Further, the primary amino acid sequence of the FGF may be augmented by derivatization using sugar moieties (glycosylation) or by other supplementary molecules such as lipids, phosphate, acetyl groups and the like. It may also be augmented by conjugation with saccharides. Certain aspects of such augmentation are accomplished through post-transnational processing systems of the producing host; other such modifications may be introduced in vitro. In any event, such modifications are included in the definition of FGF used herein so long as the activity of the FGF is not destroyed. It is expected that such modifications may quantitatively or qualitatively affect the activity, either by enhancing or diminishing the activity of the FGF, in the various assays. Further, individual amino acid residues in the chain may be modified by oxidation, reduction, or other derivatization, and the FGF may be cleaved to obtain fragments that retain activity. Such alterations that do not destroy activity do not remove the polypeptide sequence from the definition of polypeptide of interest as used herein.

The art provides substantial guidance regarding the preparation and use of FGF variants. In preparing the FGF variants, one of skill in the art can readily determine which modifications to the native protein nucleotide or amino acid sequence will result in a variant that is suitable for use as a therapeutically active component of a stabilized liquid or lyophilized formulation of the present invention and whose oxidation in the formulation is decreased by the presence of a reducing agent, as disclosed herein. Examples of FGF polypeptides as well as variants and fragments thereof are known in the art. For example, see U.S. Pat. Nos. 5,989,866; 5,925,528; 5,874,254; 5,852,177; 5,817,485; 5,714,458; 5,656,458; 5,604,293; 5,576,288; 5,514,566; 5,482,929; 5,464,943; and 5,439,818; herein incorporated by reference.

In one embodiment, the stabilized liquid or lyophilized FGF formulation comprises FGF-2, also known as basic FGF, preferably recombinant FGF-2. By "recombinant FGF-2" is intended FGF-2 having comparable biological activity to native-sequence FGF-2 and which has been prepared by recombinant DNA techniques, or mutationally altered FGF-2. In general, the gene coding for FGF-2 is cloned and then expressed in transformed organisms, preferably a microorganism. The host organism expresses the foreign gene to produce FGF-2 under expression conditions. Synthetic recombinant FGF-2 can also be made in eukaryotes, such as yeast or human cells. Where the FGF is FGF-2, it may be the 146 amino acid form, the 153-155 amino acid form, or a mixture thereof depending upon the method of recombinant production. See U.S. Pat. No. 5,143,829, herein incorporated by reference. For examples of FGF-2 proteins and variants thereof, see U.S. Pat. Nos. 5,155,214; 5,859,208; and the recombinant FGF-2 muteins described in U.S. Pat. No. 5,852,177; all of which are herein incorporated by reference.

In one embodiment, the FGF-2 is the 146 amino acid bovine FGF-2 shown in SEQ ID NO: 2 or the 155 amino acid bovine FGF-2 shown in SEQ ID NO:4. In an alternate embodiment, the FGF-2 is the 146 amino acid human polypeptide shown in SEQ ID NO:1 or the 155 amino acid human polypeptide shown in SEQ ID NO:3. See U.S. Pat. No. 5,143,829, herein incorporated by reference. However, any FGF-2, or a biologically active (e.g., mitogenic or angiogenic) fragment or mutein thereof, may be utilized in the compositions of the invention. See, for example, U.S. Pat. Nos. 5,859,208 and 5,852,177, herein incorporated by reference.

The 146-residue mammalian FGF-2 set forth in SEQ ID NO:2, which is of bovine origin, like the corresponding 146-residue human FGF-2 (SEQ ID NO:1) is initially synthesized in vivo as a polypeptide having 155 amino acids (Abraham et al. (1986) *Embo J.* 5(10):2523-2528). The 155 amino acid bovine FGF-2 polypeptide is shown in SEQ ID NO:4, while the 155 amino acid human FGF-2 polypeptide is shown in SEQ ID NO:3. When compared to the full-length 155 residue FGF-2 molecules, the 146 residue FGF-2 molecules lack the first nine amino acid residues (residues 1-9 of the full-length FGF-2 of SEQ ID NO:3 and SEQ ID NO:4). The 155-residue FGF-2 of bovine or human origin, and biologically active variants thereof, can also be used in the compositions and methods of the present invention in the manner described for the bovine and human 146-residue FGF-2 molecules. Again, it is recognized that the 155-residue form may exist as 153-155 residues, or mixtures thereof, depending upon the method of recombinant protein production. The bovine FGF-2 of SEQ ID NO:2 differs from human FGF-2 in two residue positions. In particular, the amino acids at residue positions 112 and 128 of the bovine FGF-2 of SEQ ID NO:2 (which correspond to positions 121 and 137 or SEQ ID NO:4) are Ser and Pro, respectively, whereas amino acids 112 and 128 of the human FGF-2 polypeptide of SEQ ID NO:1 (which correspond to positions 121 and 137 of SEQ ID NO:3) are Thr and Ser, respectively.

The pharmaceutical compositions and methods of the invention can utilize the 146-residue FGF-2 polypeptides of SEQ ID NO:1 or SEQ ID NO:2, and the 155-residue FGF-2 polypeptides of SEQ ID NO:3 or SEQ ID NO:4, as well as a "biologically active fragment" of any of these polypeptide. By "biologically active fragment of the polypeptide of SEQ ID NO:1, SEQ ID NO:2, SEQ ID NO:3, or SEQ ID NO:4" is intended a fragment of FGF-2 that has about 80%, 85%, 90%, 95% or more of the 146 residues of SEQ ID NO:1 or SEQ ID NO:2 or the 155 residues of SEQ ID NO:3 or SEQ ID NO:4, and that retains the biological activity of the FGF-2 of SEQ ID NO:1, SEQ ID NO:2, SEQ ID NO:3, or SEQ ID NO:4.

In order to be active in promoting cell proliferation, the FGF-2 fragment should have two cell binding sites and at least one of the two heparin binding sites. The predicted cell binding sites of human FGF-2 occur at residue positions 36-39 and 77-81 of SEQ ID NO:1, corresponding to positions 45-48 and 86-90 of SEQ ID NO:3. See Yoshida et al. (1987) *Proc. Natl. Acad. Sci. USA* 84:7305-7309). The two predicted heparin binding sites of human FGF-2 occur at residue positions 18-22 and 107-111 of SEQ ID NO:1, corresponding to positions 27-31 and 116-120 of SEQ ID NO:3. See Yoshida et al., supra. Given the substantial similarity between the amino acid sequences for human FGF-2 and bovine FGF-2, it is expected that the cell binding sites for bovine FGF-2 are also at residue positions 36-39 and 77-81 of SEQ ID NO:2 (corresponding to 45-48 and 86-90 of SEQ ID NO:4), and that the heparin binding sites are at residue positions 18-22 and 107-111 of SEQ ID NO:2 (corresponding to 27-31 and 116-120 of SEQ ID NO:4). Consistent with the above, it is well known in the art that N-terminal truncations of the FGF-2 set forth in SEQ ID NO:2 do not eliminate its angiogenic activity in cows. In particular, the art discloses several naturally occurring and biologically active fragments of FGF-2 that have N-terminal truncations relative to the FGF-2 of SEQ ID NO:2. An active and truncated FGF-2 having residues 12-146 of SEQ ID NO:2 was found in bovine liver and another active and truncated FGF-2, having residues 16-146 of SEQ ID NO:2 was found in the bovine kidney, adrenal glands, and testes. See U.S. Pat. No. 5,155,214 at col. 6, lines 41-46, citing to Ueno, et al. (1986) *Biochem. Biophys. Res. Comm.* 138:580-588. Likewise, other fragments of the bovine FGF-2 of SEQ ID NO:2 that are known to have FGF-2 activity are FGF-2 (24-120)-OH and FGF-2 (30-110)-NH$_2$ (U.S. Pat. No. 5,155,214, herein incorporated by reference). These latter fragments retain both of the cell binding portions of FGF-2 (SEQ ID NO:2) and one of the heparin binding segments (residues 107-111). Accordingly, the biologically active fragments of a mammalian FGF-2 typically encompass those terminally truncated fragments of an FGF-2 that have at least residues that correspond to residues 30-110 of FGF-2 of SEQ ID NO:2; more typically, at least residues that correspond to residues 18-146 of the polypeptide of SEQ ID NO:2.

The compositions and methods of the present invention can also utilize a "biologically active mutein" of the FGF-2 shown in SEQ ID NO:1, SEQ ID NO:2, SEQ ID NO:3, or SEQ ID NO:4. By the term "biologically active mutein" is intended a mutated form of the FGF-2 of SEQ ID NO:1, SEQ ID NO:2, SEQ ID NO:3, or SEQ ID NO:4 that structurally retains at least 80%, at least 85%, at least 90%, or at least 95% or more of the 146 residues of the human FGF-2 sequence shown in SEQ ID NO: 1, the 146 residues of the bovine FGF-2 sequence shown in SEQ ID NO:2, the 155 residues of the human FGF-2 sequence shown in SEQ ID NO:3, or the 155 residues of the bovine FGF-2 sequence in SEQ ID NO:4, respectively, in their respective positions, and that functionally retains the mitogenic or angiogenic activity of the FGF-2 of these reference sequences. Preferably, the mutations are "conservative substitutions" using L-amino acids, wherein one amino acid is replaced by another biologically similar amino acid. Examples of conservative substitutions include the substitution of one hydrophobic residue such as Ile, Val, Leu, Pro, or Gly for another, or the substitution of one charged or polar residue for another, such as between Arg and Lys, between Glu and Asp, or between Gln and Asn, and the like. Generally, the charged amino acids are considered interchangeable with one another. However, to make the substitution more conservative, one takes into account both the size and the likeness of the charge, if any, on the side chain. Other suitable substitutions include the substitution of serine or threonine for one or both of the cysteines at residue positions 87 and 92 of SEQ ID NO:1 and SEQ ID NO:2, or for residue positions 96 and 101 of SEQ ID NO:3 and SEQ ID NO:4, which are not involved in disulfide formation. Other suitable substitutions include any substitution wherein at least one constituent cysteine is replaced by another amino acid so that the mutein has greater stability under acidic conditions; see U.S. Pat. No. 5,852,177, which is herein incorporated by reference. One such substitution is the replacement of cysteine residues with neutral amino acids such as for example: glycine, valine, alanine, leucine, isoleucine, tyrosine, phenylalanine, histidine, tryptophan, serine, threonine, and methionine (U.S. Pat. No. 5,852,177). Preferably, substitutions are introduced at the FGF-2 N-terminus, which is not associated with mitogenic or angiogenic activity. However, as discussed above, conservative substitutions are suitable for introduction throughout the molecule.

Recombinant mammalian FGF-2, or a biologically active fragment or variant may be made, for example, as described in U.S. Pat. Nos. 5,155,214, 5,439,616, and 5,656,458, which are incorporated herein by reference in their entirety. As disclosed in the '214 patent, a nucleotide sequence encoding FGF-2 is inserted into a cloning vector, such as pBR322, pMB9, Col E1, pCRI, RP4 or λ-phage, and the cloning vector is used to transform either a eukaryotic or prokaryotic cell, wherein the transformed cell expresses the FGF-2. The coding sequences for human and bovine 146 and 155 amino acid residue FGF-2 are known and set forth herein as SEQ ID NO:5, SEQ ID NO:6, SEQ ID NO:7, and SEQ ID NO:8, respectively. In one embodiment, the host cell is a yeast cell, such as *Saccharomyces cerevisiae*. In some embodiments, the expressed FGF-2 has 146 amino acids in accordance with SEQ ID NO:1 or SEQ ID NO:2, while in other embodiments the expressed FGF-2 has 155 amino acids in accordance with SEQ ID NO:3 or SEQ ID NO:4. Although the FGF-2's of SEQ ID NOS:1-4 have four cysteines, i.e. at positions 25, 69, 87, and 92 of SEQ ID NOS:1 and 2, corresponding to positions 34, 78, 96, and 101 of SEQ ID NOS:3 and 4, there are no internal disulfide linkages ('214 at col. 6, lines 59-61). However, in the event that cross-linking occurs under oxidative conditions, it would likely occur between the residues at positions 25 and 69 of SEQ ID NOS:1 and 2 or 34 and 78 of SEQ ID NOS:3 and 4. Thus the pharmaceutical formulations of the invention comprise an FGF of interest, for example FGF-2, and a reducing agent in an amount sufficient to inhibit oxidation of this therapeutically active polypeptide. It is further noted that these pharmaceutical formulations do not exhibit clinically relevant hemolytic activity. By "clinically relevant hemolytic activity" is intended hemolysis greater than about 10% as detected in a sample of whole blood mixed with a particular test vehicle of interest, in this case a pharmaceutical formulation of the invention. Generally, as a point of reference, the percent hemolysis of distilled water plus whole blood is 100%. Thus, when a whole blood sample from a subject is mixed with a pharmaceutical formulation of the invention, the detectable level of hemolysis is less than about 10%, preferably less than about 5%, more preferably less than about 4%, 3%, 2%, or 1%. For purposes of the present invention, such pharmaceutical formulations as said to have a hemolytic potential of less than about 10%, preferably less than about 5%, more preferably less than about 4%, 3%, 2%, or 1% when direct contact is made with the blood of a subject following administration of the formulation. As a result, the pharmaceutical compositions of the invention can safely be administered to a subject without adverse hemolytic consequences, and furthermore, are compatible with plasma and serum. Methods for detection of hemolytic activity of a test vehicle are known in the art. See, for example, the method disclosed in O'Leary et al. (1996) *J. Pharm. Sci.* 58:1007-1010, herein incorporated by reference, and Example 4 below. A pharmaceutically effective amount of a stabilized liquid FGF pharmaceutical formulation, or of a reconstituted stabilized lyophilized FGF pharmaceutical formulation of the invention is administered to a subject. By "pharmaceutically effective amount" is intended an amount that is useful in the treatment, prevention or diagnosis of a disease or condition. Typical routes of administration include, but are not limited to, oral administration and parenteral administration, including intravenous, intramuscular, subcutaneous, intraarterial and intraperitoneal injection or infusion. In one such embodiment, the administration is by injection, preferably subcutaneous injection. Injectable forms of the compositions of the invention include, but are not limited to, solutions, suspensions and emulsions.

The stabilized liquid pharmaceutical composition comprising the FGF polypeptide of interest should be formulated in a unit dosage and may be in an injectable or infusible form such as solution, suspension, or emulsion. Furthermore, it can be stored frozen or prepared in the dried form, such as a lyophilized powder, which can be reconstituted into the liquid solution, suspension, or emulsion before administration by any of various methods including oral or parenteral routes of administration. The stabilized pharmaceutical composition is preferably sterilized by membrane filtration and is stored in unit-dose or multi-dose containers such as sealed vials or ampules. Additional methods for formulating a pharmaceutical composition generally known in the art may be used to further enhance storage stability of the liquid pharmaceutical compositions disclosed herein provided they do not adversely affect the beneficial effects of the preferred stabilizing and buffering agents disclosed in the methods of the invention. A thorough discussion of formulation and selection of pharmaceutically acceptable carriers, stabilizers, etc. can be found in *Remington's Pharmaceutical Sciences* (1990) (18th ed., Mack Pub. Co., Eaton, Pa.), herein incorporated by reference.

By "subject" is intended any animal. Preferably the subject is mammalian, must preferably the subject is human. Mammals of particular importance other than human include, but are not limited to, dogs, cats, cows, horses, sheep, and pigs.

When administration is for the purpose of treatment, administration may be for either a prophylactic or therapeutic purpose. When provided prophylactically, the substance is provided in advance of any symptom. The prophylactic administration of the substance serves to prevent or attenuate any subsequent symptom. When provided therapeutically, the substance is provided at (or shortly after) the onset of a symptom. The therapeutic administration of the substance serves to attenuate any actual symptom.

The present invention also provides a method for increasing stability of an FGF polypeptide in a liquid or lyophilized pharmaceutical formulation, where the FGF becomes oxidized during storage in a liquid or lyophilized formulation. The method comprises incorporating a reducing agent into the liquid or lyophilized formulation in an amount sufficient to decrease oxidation of FGF-2 during storage of the liquid or lyophilized formulation. This formulation can then be mixed with any suitable buffer as described herein.

Increasing stability of an FGF or variant thereof by incorporating a reducing agent, or a reducing agent plus one or more additional stabilizing agents described herein, leads to an increase in stability of the liquid or lyophilized FGF-containing composition during storage. Thus, the invention also provides a method for increasing storage stability of a liquid or lyophilized pharmaceutical formulation when that composition comprises an FGF that oxidizes during storage in a liquid or lyophilized formulation. By "increasing storage stability" is intended the composition exhibits greater retention of the FGF or variant thereof in its proper, reduced, biologically active conformation during storage, and thus less of a decline in biological activity, than does a liquid or lyophilized composition prepared in the absence of a reducing agent, or a reducing agent plus one or more of the additional stabilizing agents described herein.

Storage stability of an FGF-containing pharmaceutical compositions made in accordance with the methods of the invention can be assessed using standard procedures known in the art. Typically, storage stability of such compositions is assessed using storage stability profiles. These profiles are obtained by monitoring changes in the amount of FGF present in its reduced, biologically active molecular form and its potency over time in response to the variable of interest, such as pH, concentration, stabilizing agent, concentration of stabilizing agent, etc., as demonstrated in the Examples below. These stability profiles can be generated at several temperatures representative of possible storage conditions, such as freezing temperature, refrigerated temperature, room temperature, or elevated temperature, such as at 40-50° C. Storage stability is then compared between profiles by determining, for example, percentage of the reduced, biologically active molecular form of the FGF of interest that is retained in the sample, which is assayed by, for example, the percentage of main peak in RP-HPLC analysis. FGF lyophilized pharmaceutical formulations comprising a reducing agent prepared in accordance with the methods of the present invention will retain at least about 90% of the FGF in the reduced form when stored at 2-8° C. for at least about 18 months. See FIG. 7 and Example 3 below. For purposes of the present invention, a composition having increased storage stability as a result of being prepared in accordance with the present invention is considered a "stabilized" pharmaceutical composition.

The following examples are offered by way of illustration and not by way of limitation.

EXPERIMENTAL

FGF-2 is a growth factor that promotes tissue regeneration. It has wide therapeutic application for example as a treatment for wound healing and for ischemic heart diseases. Other therapeutic uses for FGF-2 include PAD, bone fracture healing, and stroke. This protein exhibits oxidation in pharmaceutical formulations contributing to a decline in potency with storage.

A new stabilized FGF-2 formulation has been developed. This formulation comprises FGF-2 and at least one reducing agent in an amount sufficient to inhibit FGF oxidation. A suitable buffering agent and other stabilizing agents, such as sucrose, glycine, and EDTA, may also be included. As shown in the following examples, addition of the reducing agents of the invention to the FGF-2 formulation increases its storage stability.

The FGF-2 molecule used in these examples is the recombinant human FGF-2 having the sequence set forth in SEQ ID NO:1. Methods for recombinant production of human FGF-2 are known in the art as noted elsewhere herein. See, for example, The following protocols were used in the examples to determine the effect of a particular reducing agent on FGF-2 stability.

RP-HPLC

Reversed Phase HPLC (RP-HPLC) was performed using a Waters 600S controller and a Waters 717 autosampler. Separations were accomplished on a Zorbax 300SB-CN, 4.6 mm ID×15 cm, 5:, cyano column with sample detection at 214 nm on a Waters 486 UV detector. Samples were run at 1.0 mL/min and injection volumes were 50 μL (~15 μg of protein per injection). Elution was achieved with a gradient of acetonitrile/water/0.1% TFA from approximately 6% ACN (30%-36%).

pH Measurement

The solution pH of the various formulations was measured by a pH meter from Orion (Model 611, Orion Research Incorporated Laboratory Products Group, Boston, Mass.). The pH meter was calibrated by the two-buffer calibration procedure suggested by the manufacturer using a pH 4 standard (Fisher Scientific, Cat. No. SB 101-500) and a pH 7 standard (Fisher Scientific, Cat. No. SB 107-500).

Lyophilization rhFGF-2 was lyophilized using the following cycle: Vials were placed on pre-cool shelves set at 10° C. The shelf temperature was ramped at 40° C./hour to −50° C. where the vials were frozen for 2 hours. The temperature of the shelves was then ramped at 40° C. per hour to −25° C. and held for 2 hours to crystallize the glycine in the formulation. A vacuum of 50 μm was then initiated, and primary drying was accomplished over 32 hours. After primary drying was complete, the shelf temperature was ramped at 25° C./hour to 40° C. for 8 hours. The temperature was then reduced to 4° C. and the vials were stoppered and capped.

Example 1

Effects of Various Concentrations of DTT on FGF-2 Stability

Much of FGF-2 instability in pharmaceutical formulations can be attributed to oxidation. The stability of FGF-2 in different formulations can be quantitated by measuring the retention of the main peak using RP-HPLC. This main peak corresponds to the FGF-2 that remains in the reduced form.

Using the analytical procedures described herein, the storage stability of FGF-2 under several conditions was followed by monitoring changes in the RP-HPLC main peak as a function of storage time at 4° C., 17° C., and 30° C.

Experiments were conducted to determine the appropriate levels of dithiothreitol (DTT) required for maximum stability of FGF-2 formulations. Concentrations of DTT from 0 to 10 mM were examined in formulations between pH 5.5 and pH 6.5. The formulations in this experiment are shown in Table 1.

TABLE 1

Formulations used to determine the stabilizing effect of various concentrations of DTT and the pH.

| | Sodium Citrate | Glycine | Sucrose | Acetyl cysteine | EDTA | DTT | pH |
|---|---|---|---|---|---|---|---|
| 1 | 10 mM | 2% | 1% | 0.5% | 1 mM | 0 mM | 5.5 |
| 2 | 10 mM | 2% | 1% | 0.5% | 1 mM | 0.1 mM | 5.5 |
| 3 | 10 mM | 2% | 1% | 0.5% | 1 mM | 1 mM | 5.5 |
| 4 | 10 mM | 2% | 1% | 0.5% | 1 mM | 10 mM | 5.5 |
| 5 | 10 mM | 2% | 1% | 0.5% | 1 mM | 0 mM | 6.0 |
| 6 | 10 mM | 2% | 1% | 0.5% | 1 mM | 0.1 mM | 6.0 |
| 7 | 10 mM | 2% | 1% | 0.5% | 1 mM | 1 mM | 6.0 |
| 8 | 10 mM | 2% | 1% | 0.5% | 1 mM | 10 mM | 6.0 |
| 9 | 10 mM | 2% | 1% | 0.5% | 1 mM | 0 mM | 6.5 |
| 10 | 10 mM | 2% | 1% | 0.5% | 1 mM | 0.1 mM | 6.5 |
| 11 | 10 mM | 2% | 1% | 0.5% | 1 mM | 1 mM | 6.5 |
| 12 | 10 mM | 2% | 1% | 0.5% | 1 mM | 10 mM | 6.5 |

In this example, all formulations were liquids and were produced from the same lot of bulk drug. Formulations were stored at 4° C., 17° C., and 30° C. As increasing temperature can accelerate the degradation of FGF-2, one would expect that formulations stored at 30° C. would degrade faster than those at 17° C. or 4° C. Stability of the formulations was assessed by a number of assays. Reverse Phase HPLC (RP-HPLC) is the most sensitive method used and gives the most relevant information about the stability of FGF-2. When the cysteine residues of FGF-2 oxidize, the increase in oxidation results in a decrease in the % Main Peak for the RP-HPLC profile.

Figure 2:
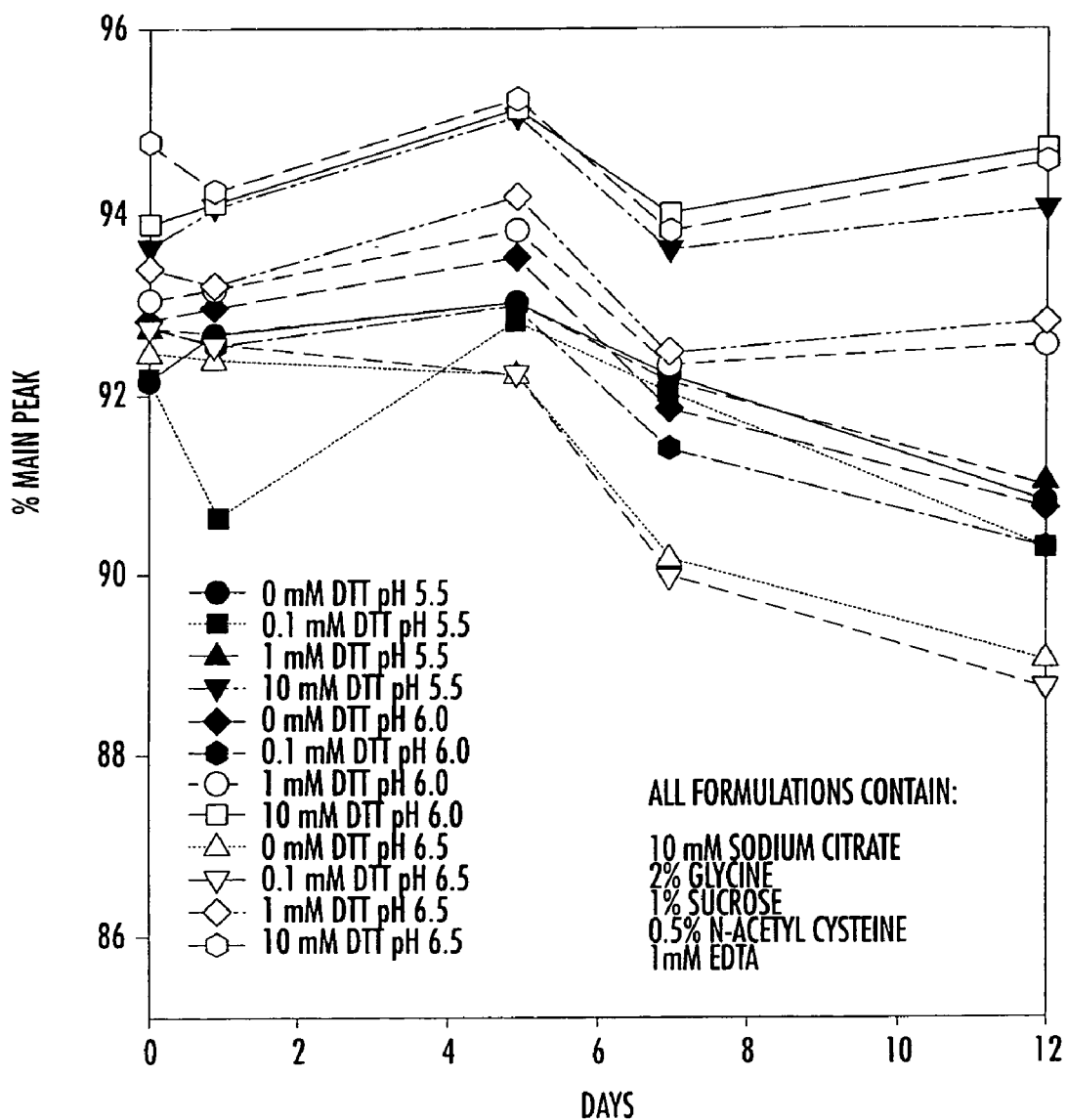
FIG. 2 shows the percentage of the main peak remaining during storage of the different liquid FGF-2 formulations at 17° C. The formulations contain 10 mM sodium citrate, 2% glycine, 1% sucrose, 0.5% n-acetyl cysteine, 1 mM EDTA, and DTT in a concentration of 0 mM, 0.1 mM, 1 mM, or 10 mM. Each formulation was tested for stability at pH 5.5, 6.0, and 6.5.
Figure 3:
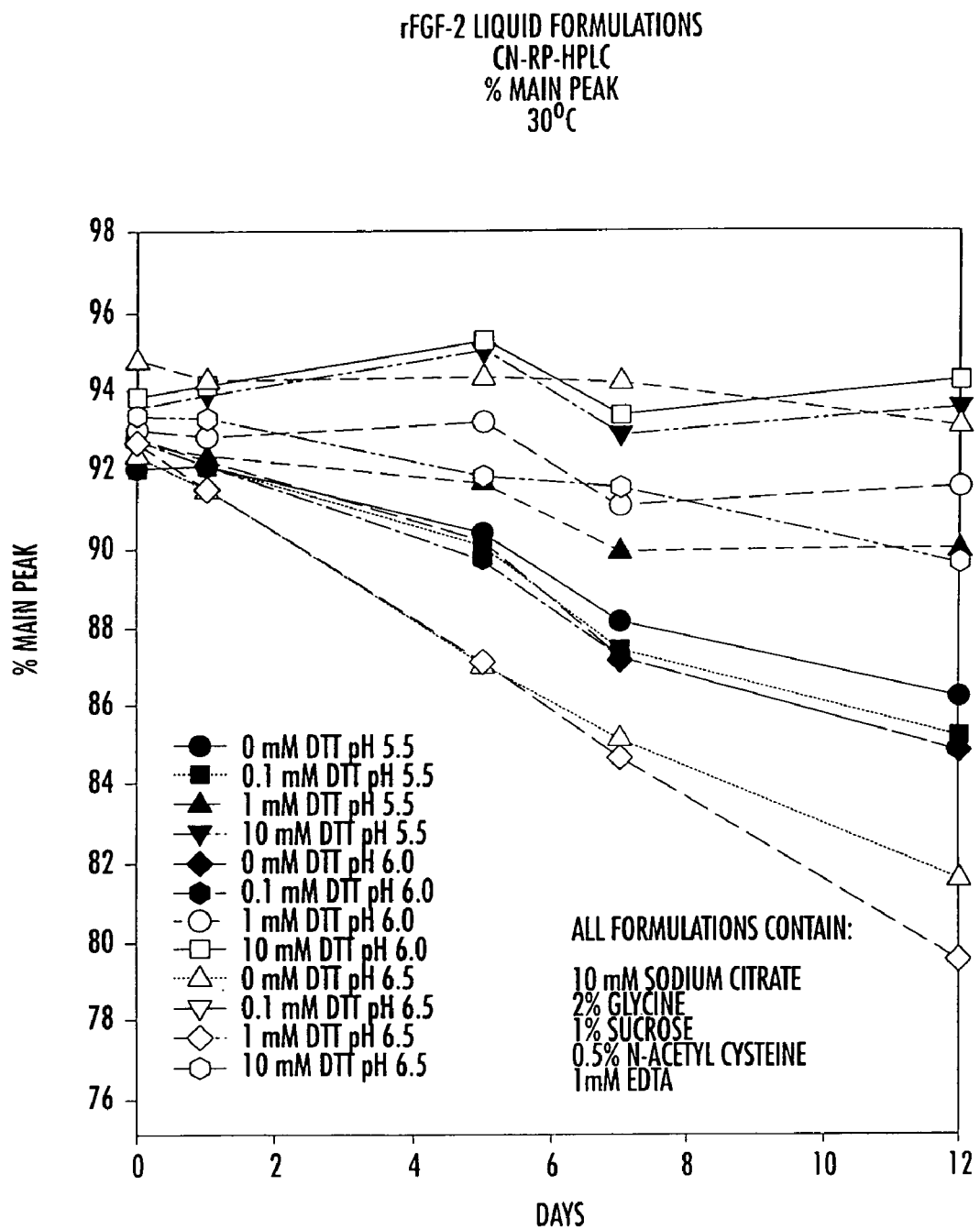
FIG. 3 shows the percentage of the main peak remaining during storage of the different liquid FGF-2 formulations at 30° C. The formulations contain 10 mM sodium citrate, 2% glycine, 1% sucrose, 0.5% n-acetyl cysteine, 1 mM EDTA, and DTT in a concentration of 0 mM, 0.1 mM, 1 mM, or 10 mM. Each formulation was tested for stability at pH 5.5, 6.0, and 6.5.

RP-HPLC results for these studies are shown in FIGS. 1-3. These data indicate that DTT protects FGF-2 from oxidation in a concentration-dependent manner. Formulations at all three pH values containing 10 mM DTT were found to be more stable (higher % Main Peak) than formulations containing 1 mM DTT, which were more stable than formulations containing 0.1 or 0 mM DTT. This was most notable at storage temperatures of 17° C. and 30° C., where degradation is expected to be more rapid.

Example 2

Effects of 10 mM DTT, 0.5% N-Acetyl-Cysteine or a Combination of Both on FGF-2 Stability Experiments were carried out to determine whether DTT, n-acetyl cysteine or a combination of these two thiol derivatives would give the best stability for FGF-2 formulations. The formulations in this experiment are shown in Table 2.

TABLE 2

Formulations used to determine the stabilizing effects of DTT in combination with n-acetyl-cysteine at various pH conditions.

| | Sodium Citrate | Glycine | Sucrose | EDTA | DTT | N-Acetyl-Cysteine | pH |
|---|---|---|---|---|---|---|---|
| 1 | 10 mM | 2% | 1% | 1 mM | 0 mM | 0 | 5.5 |
| 2 | 10 mM | 2% | 1% | 1 mM | 0 mM | 0.5% | 5.5 |
| 3 | 10 mM | 2% | 1% | 1 mM | 10 mM | 0 | 5.5 |
| 4 | 10 mM | 2% | 1% | 1 mM | 0 mM | 0.5% | 5.5 |
| 5 | 10 mM | 2% | 1% | 1 mM | 0 mM | 0.5% | 6.0 |
| 6 | 10 mM | 2% | 1% | 1 mM | 10 mM | 0 | 6.0 |
| 7 | 10 mM | 2% | 1% | 1 mM | 0 mM | 0.5% | 6.0 |
| 8 | 10 mM | 2% | 1% | 1 mM | 0 mM | 0.5% | 6.5 |
| 9 | 10 mM | 2% | 1% | 1 mM | 10 mM | 0 | 6.5 |
| 10 | 10 mM | 2% | 1% | 1 mM | 10 mM | 0.5% | 6.5 |

Figure 4:
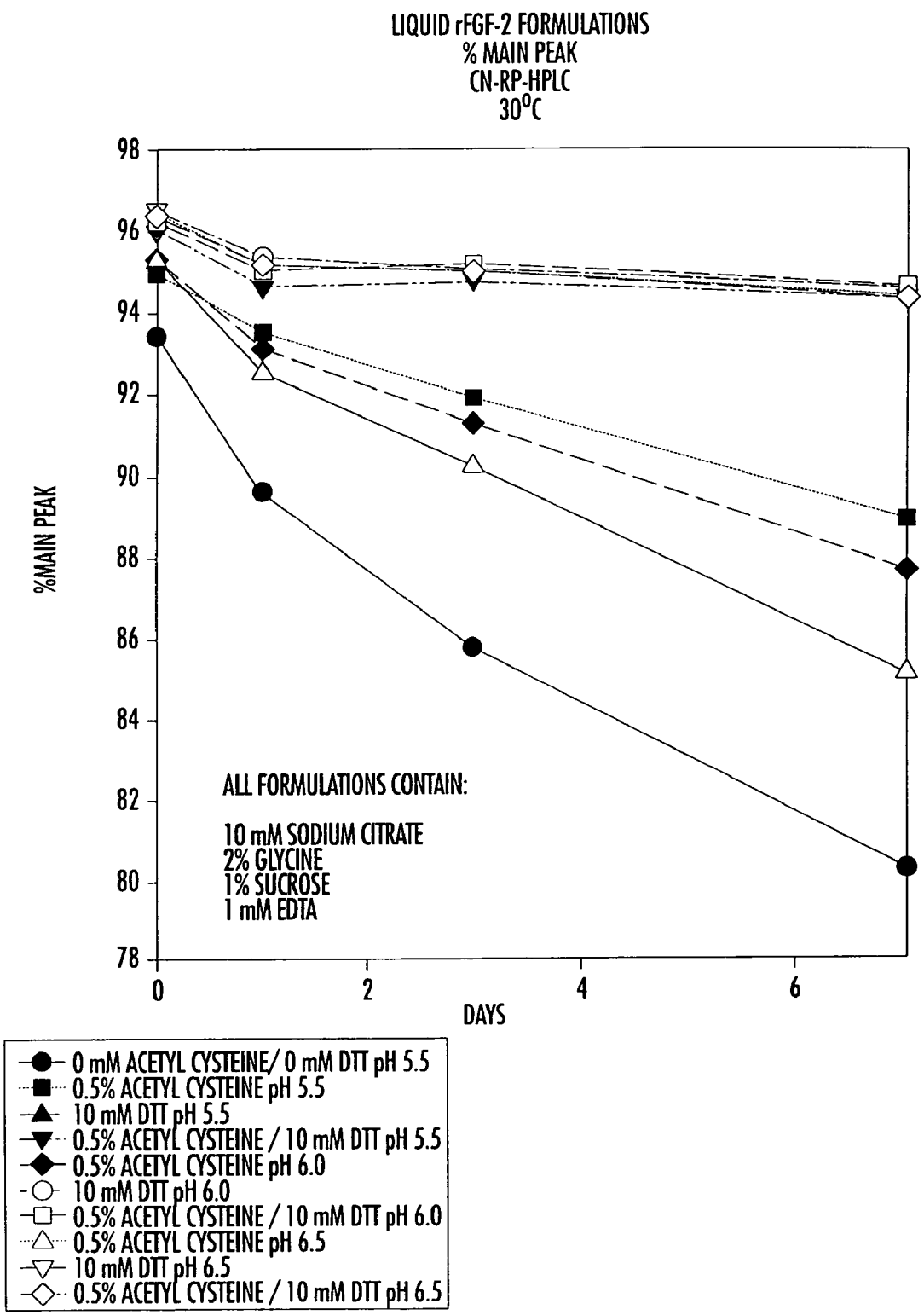
FIG. 4 shows the percentage of the main peak remaining during storage of the different liquid FGF-2 formulations at 30° C. The formulations contain 10 mM sodium citrate, 2% glycine, 1% sucrose, 1 mM EDTA, and one reducing agent selected from the following: 0.5% n-acetyl-cysteine, 10 mM DTT, both, or neither. Each formulation was tested for stability at pH 5.5, 6.0, and 6.5.

FGF-2 stability was examined in both liquid and lyophilized (freeze-dried) formulations using RP-HPLC. As in the previous study, liquid formulations were stored at 4° C., 17° C., and 30° C. Stability results at 30° C. are shown in FIG. 4. At all three pH values, formulations containing DTT (with or without n-acetyl-cysteine) were more stable than formulations that did not contain DTT. In addition, formulations containing n-acetyl cysteine (without DTT) were more stable than formulations containing no thiol derivative (i.e., reducing agent). For formulations containing n-acetyl cysteine alone, the pH 5.5 formulation was more stable than the pH 6.0 formulation, which was more stable than the pH 6.5 formulation.

Figure 5:
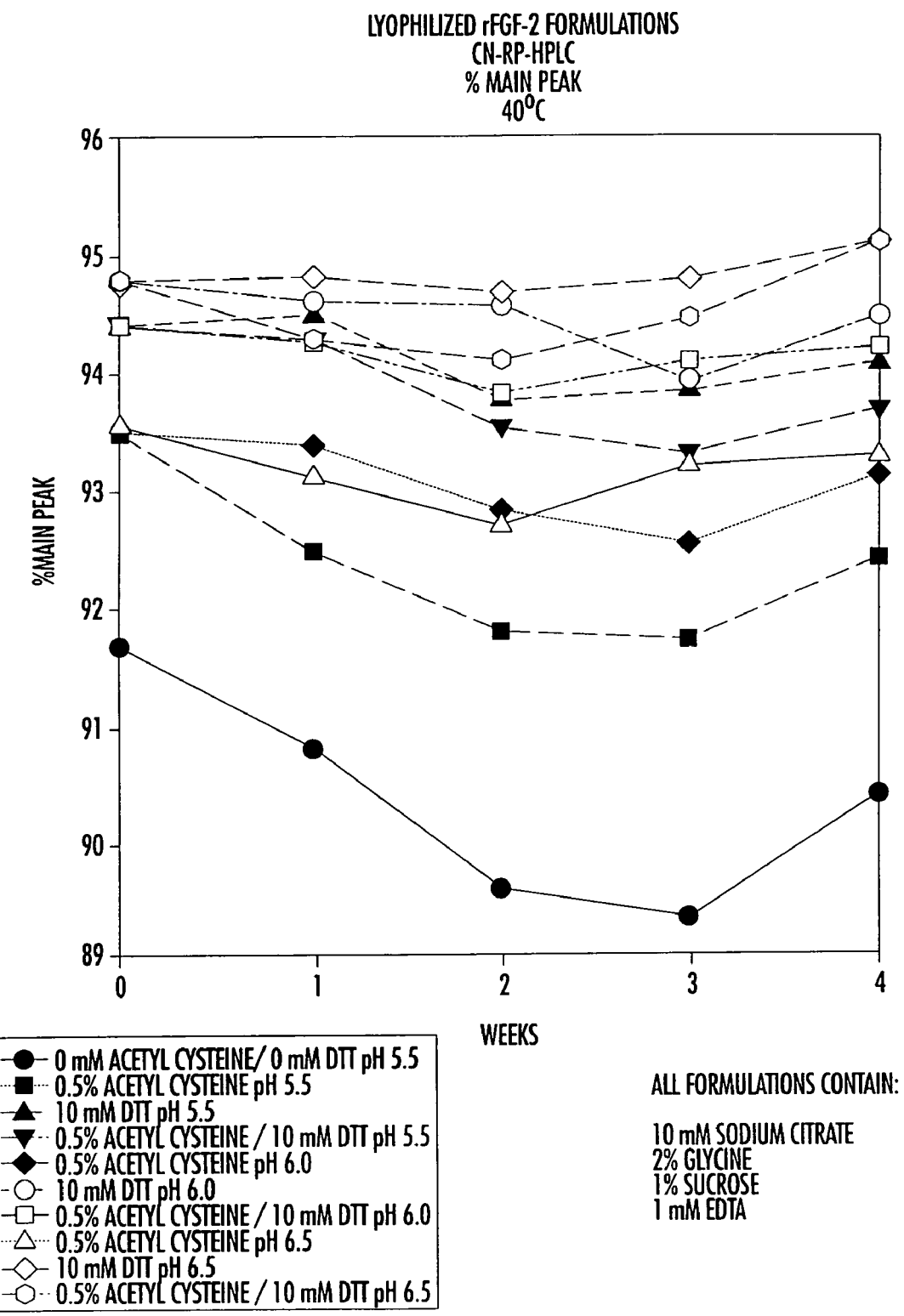
FIG. 5 shows the percentage of the main peak remaining during storage of the different lyophilized FGF-2 formulations at 40° C. The formulations contain 10 mM sodium citrate, 2% glycine, 1% sucrose, 1 mM EDTA, and one reducing agent selected from the following: 0.5% n-acetyl-cysteine, 10 mM DTT, both, or neither. Each formulation was tested for stability at pH 5.5, 6.0, and 6.5.
Figure 6:
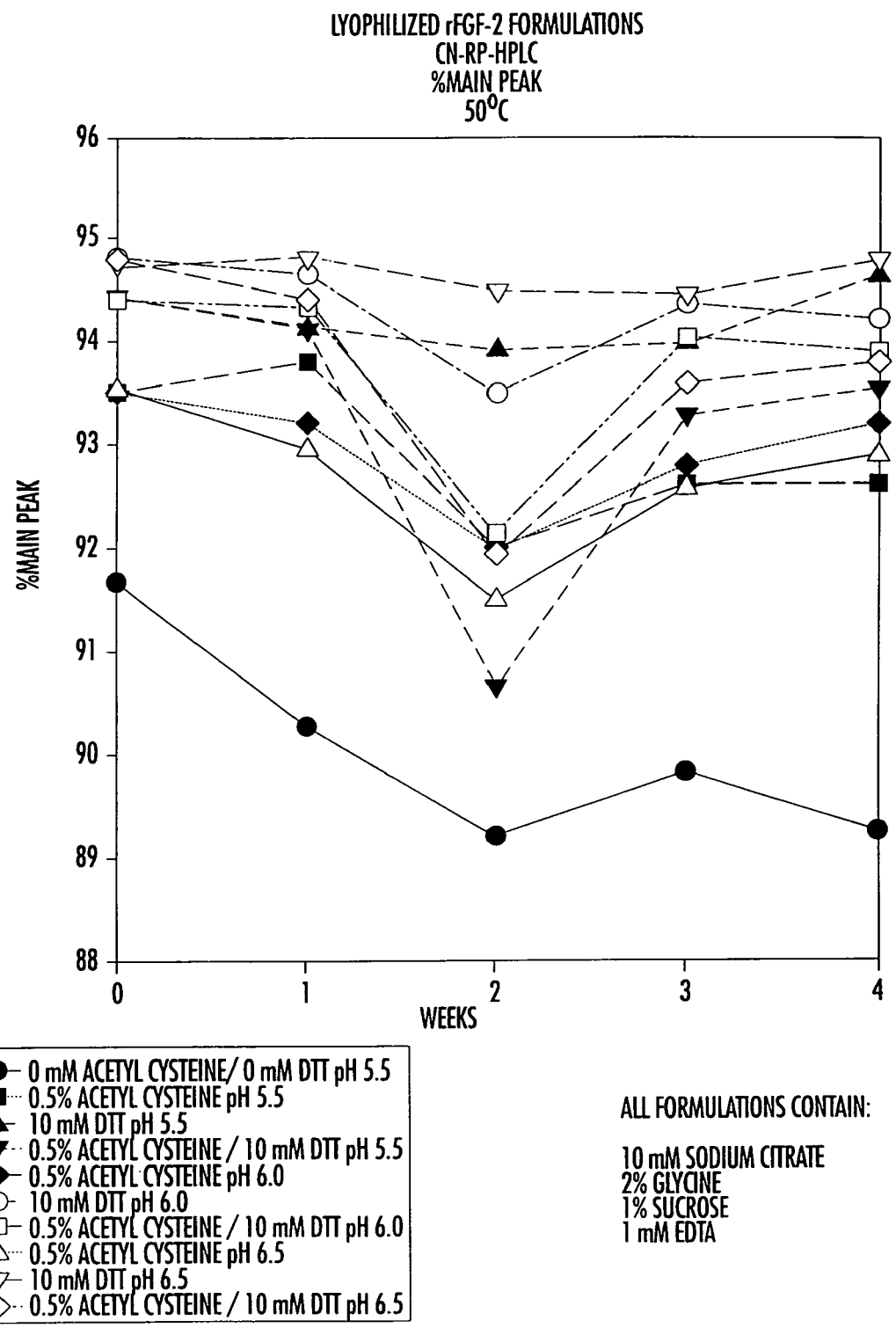
FIG. 6 shows the percentage of the main peak remaining during storage of the different lyophilized FGF-2 formulations at 50° C. The formulations contain 10 mM sodium citrate, 2% glycine, 1% sucrose, 1 mM EDTA, and one reducing agent selected from the following: 0.5% n-acetyl-cysteine, 10 mM DTT, both, or neither. Each formulation was tested for stability at pH 5.5, 6.0, and 6.5.

Lyophilized formulations were stored at 40° C. and 50° C. RP-HPLC results are shown in FIGS. 5 and 6. At 40° C., formulations containing DTT were more stable than formulations containing only n-acetyl cysteine. The formulation containing no reducing agent was less stable than all other formulations. At 50° C., where degradation is expected to be most rapid, formulations containing DTT alone were more stable than formulations containing a combination of DTT and n-acetyl cysteine. Formulations containing DTT (with or without n-acetyl cysteine) were more stable than those containing only n-acetyl cysteine. These data indicate that reducing agents, most preferably DTT, stabilize both liquid and lyophilized formulations of FGF-2.

Example 3

Stability of Lyophilized Formulations Containing DTT

To assess the long term stability of rhFGF-2, two lots of rhFGF-2 were prepared and formulated. Each lot was produced from a different lot of bulk drug (derived from separate fermentation and purification campaigns). Formulations from each lot bulk drug were prepared at 0.35 mg/ml and 3.5 mg/ml. Vials were filled and lyophilized. In addition to the rhFGF-2, the formulations contained 10 mM sodium citrate, 4% glycine, 1% sucrose, 1 mM EDTA, 10 mM DTT, pH 6.0.

Figure 7:
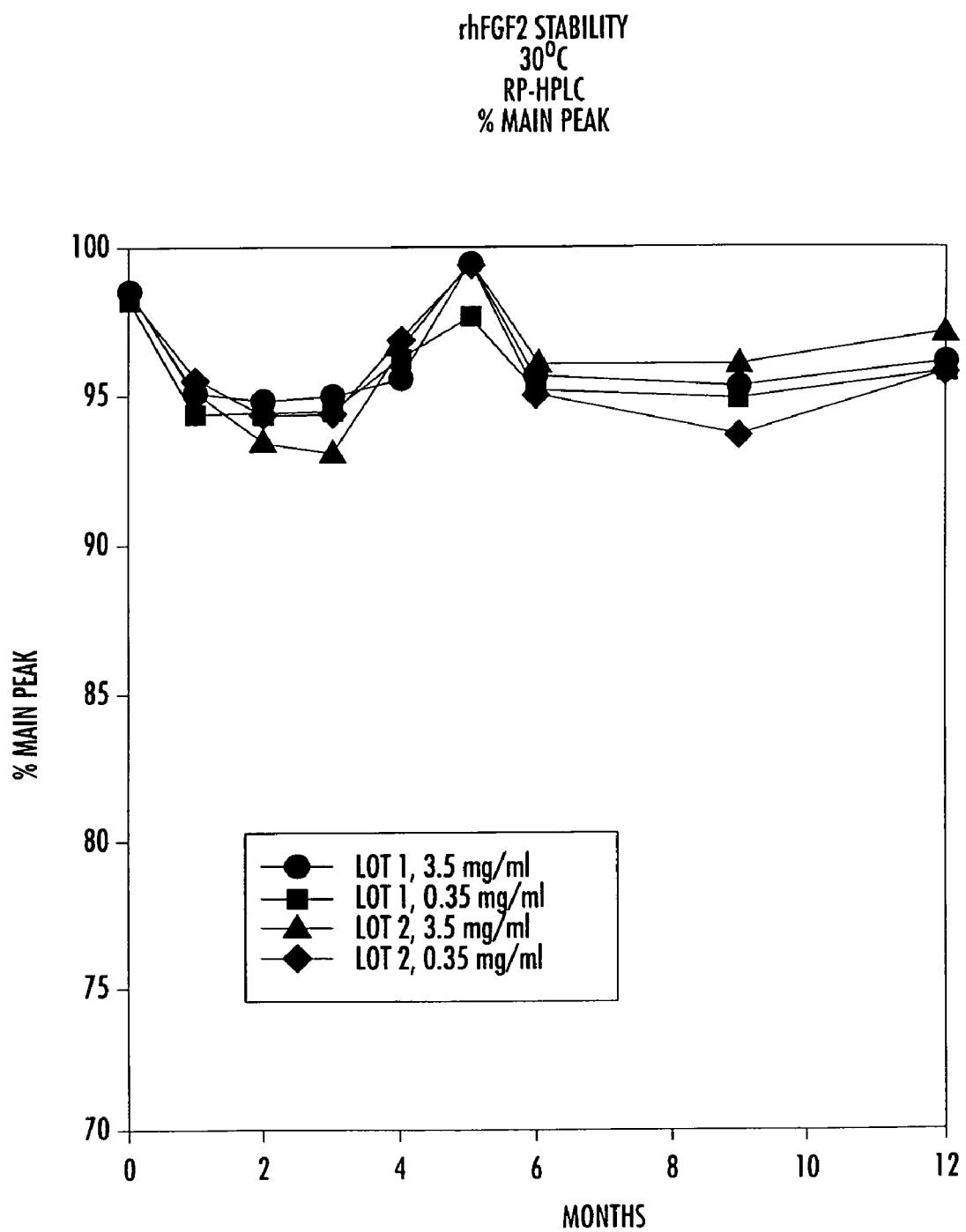
FIG. 7 shows the percentage of the main peak remaining during storage rhFGF-2 (recombinant human sequence FGF-2) formulations at 30° C. The formulations contain 10 mM sodium citrate, 4% glycine, 1% sucrose, 1 mM EDTA, 10 mM DTT, pH 6.0.

Lyophilized formulations were stored for 12 months at 4° C., 25° C. and 30° C. Stability was monitored with a number of stability indicating assays. RP-HPLC results are shown in FIG. 7 for the materials stored at 30° C. These results demonstrate that even after storage at 30° C. for 1 year, the rhFGF-2 in these formulations shows little (if any) detectable degradation. The changes observed are within the variability of the assay.

Example 4

Hemolytic Potential of Reducing Agent Formulations in Human Blood

Release of hemoglobin from lysed red blood cells has been shown to be an effective method for determining the in vivo hemolytic potential of test materials following direct contact with blood (O'Leary et al. (1969) *J. Pharm. Sci.* 58:1007-1010). Using a similar protocol, a study was undertaken to assess the hemolytic potential of pharmaceutical formulations comprising buffers having dithiothreitol (DTT), n-acetyl cysteine, and monothioglycerol in amounts sufficient to stabilize a polypeptide such as FGF within the formulation.

Three formulations were tested, designated as test articles A, B, and C, along with negative and positive controls. The test articles, and negative and positive controls were as follows:

Test Article A:

| Dithiothreitol Buffer: | 10 mM sodium citrate, 2% glycine, 1% sucrose, 10 mM DTT (FW 154.2), 1 mM disodium EDTA, pH 6.0 |
|---|---|
| Appearance: | White solid |
| Storage: | 2-8° C. |

Test Article B:

| Acetyl Cysteine Buffer: | 10 mM sodium citrate, 2% glycine, 1% sucrose, 0.5% acetyl cysteine (FW 372.2), 1 mM disodium EDTA, pH 6.0 |
|---|---|
| Appearance: | White solid |
| Storage: | 2-8° C. |

Test Article C:

| Monothioglycerol Buffer: | 10 mM sodium citrate, 10 mM monothioglycerol (FW 108.2), 0.3 mM disodium EDTA, 135 mM sodium chloride, pH 5.5 |
|---|---|
| Appearance: | Frozen solution |
| Storage: | −70° C. |

Negative Control and Diluent:

| Identity: | Saline (0.9% NaCl) |
|---|---|
| Supplier: | Abbott Labs |
| Lot Number: | 55-545-FDW |
| Storage: | Room temperature |

Positive Control (for Hemolysis):

| Identity: | De-ionized water |
|---|---|
| Supplier: | Calvert in-house system (Calvert Preclinical Services, Inc., Olyphant, Pennsylvania) |

Test Article Formation

The test articles were prepared on the day of study conduct. Test articles A and B were prepared by adding 2.25 ml of sterile water for injection USP and mixed until completely dissolved. Test article C was removed from the freezer and allowed to thaw. Each test article was diluted 1:10 and 1:20 with saline. Undiluted and 1:10 and 1:20 dilutions were used in the study.

Experimental Procedure

The test system was human blood collected from a healthy female volunteer, age 47, weighing a minimum of 110 lb. The study was carried out using the following protocols.

Hemolysis Assay:

Blood samples from an apparently healthy human female were collected in heparinized tubes. The blood sample was maintained at room temperature and tested on the day collected. One ml of each concentration of test article, negative control, or positive control was mixed with an equal volume of blood as shown in Table 3.

TABLE 3

Sample components for hemolysis assay.

| Tube | Blood (1 ml) | Water (1 ml) | Saline (1 ml) | Test Article (1 ml) |
|---|---|---|---|---|
| 1[a] | Human | − | + | − |
| 2[b] | Human | + | − | − |
| 3 | Human | − | − | A (undiluted) |
| 4 | Human | − | − | A (1:10) |
| 5 | Human | − | − | A (1:20) |
| 6 | − | − | + | A (undiluted) |
| 7 | − | − | + | A (1:10) |
| 8 | − | − | + | A (1:20) |
| 9 | Human | − | − | B (undiluted) |
| 10 | Human | − | − | B (1:10) |
| 11 | Human | − | − | B (1:20) |
| 12 | − | − | + | B (undiluted) |
| 13 | − | − | + | B (1:10) |
| 14 | − | − | + | B (1:20) |
| 15 | Human | − | − | C (undiluted) |
| 16 | Human | − | − | C (1:10) |
| 17 | Human | − | − | C (1:20) |
| 18 | − | − | + | C (undiluted) |
| 19 | − | − | + | C (1:10) |
| 20 | − | − | + | C (1:20) |

+ = added to tube
− = not added to tube
[a] = negative control for hemolysis
[b] = negative control for hemolysis
Test Article A = Dithiothreitol Buffer
Test Article B = Acetyl Cysteine Buffer
Test Article C = Monothioglycerol Buffer Tubes were gently mixed and incubated for 45 minutes at 37° C.±2°. After incubation, the tubes were centrifuged for 5 minutes at 1000 g. The amount of hemoglobin in the supernatant of each sample was analyzed spectrophotometrically at 540 nm.

Flocculation Assay:

Blood samples from an apparent healthy human female were collected in both heparinized tubes and tubes without an anticoagulant. The blood was processed to obtain plasma and serum. The plasma and serum were used on the day collected. One ml of each concentration of test or control article was mixed with an equal volume of plasma, serum and saline as shown in Table 4.

TABLE 4

Sample components for flocculation assay.

| Tube | Blood (1 ml) | Water (1 ml) | Saline (1 ml) | Test Article (1 ml) |
|---|---|---|---|---|
| 1[a] | Human | − | + | − |
| 2 | Human | − | − | A (undiluted) |
| 3 | Human | − | − | A (1:10) |
| 4 | Human | − | − | A (1:20) |
| 5 | − | Human | − | A (undiluted) |
| 6 | − | Human | − | A (1:10) |
| 7 | − | Human | − | A (1:20) |
| 8 | − | − | + | A (undiluted) |
| 9 | − | − | + | A (1:10) |
| 10 | − | − | + | A (1:20) |
| 11 | Human | − | − | B (undiluted) |
| 12 | Human | − | − | B (1:10) |
| 13 | Human | − | − | B (1:20) |
| 14 | − | Human | − | B (undiluted) |
| 15 | − | Human | − | B (1:10) |
| 16 | − | Human | − | B (1:20) |
| 17 | − | − | − | B (undiluted) |
| 18 | − | − | + | B (1:10) |
| 19 | − | − | + | B (1:20) |

TABLE 4-continued

Sample components for flocculation assay.

| Tube | Blood (1 ml) | Water (1 ml) | Saline (1 ml) | Test Article (1 ml) |
|---|---|---|---|---|
| 20 | Human | – | – | C (undiluted) |
| 21 | Human | – | – | C (1:10) |
| 22 | Human | – | – | C (1:20) |
| 23 | – | Human | – | C (undiluted) |
| 24 | – | Human | – | C (1:10) |
| 25 | – | Human | – | C (1:20) |
| 26 | – | – | + | C (undiluted) |
| 27 | – | – | + | C (1:10) |
| 28 | – | – | + | C (1:20) |

+ = ml added to tube
– = not added to tube
$a$ = negative control for flocculation
Test Article A = Dithiothreitol Buffer
Test Article B = Acetyl Cysteine Buffer
Test Article C = Monothioglycerol Buffer Tubes were gently mixed and incubated for 30 minutes at room temperature. After incubation, the tubes were examined macroscopically and microscopically for precipitation or coagulation. An aliquot from each tube was centrifuged at 14,000 rpm in a microcentrifuge for 10 minutes. Each tube was examined for the presence or absence of a pellet. The presence of a reddish pellet (presumably blood cells that are inadvertently carried over subsequent to the lower speed centrifugation for serum/plasma separation) is not considered a sign of incompatibility.

Data Evaluation

Hemolysis Assay:

The percent hemolysis was determined by the formula:

$$\% \text{ Hemolysis} = \frac{\text{Abs. of } TA \text{ or vehicle w/blood} - \text{Abs. of saline w/blood} - \text{Abs. of } TA \text{ or vehicle}}{\text{Abs. of water w/blood} - \text{Abs. of saline w/blood}} \times 100$$

The percent hemolysis of distilled water plus blood is 100%. Hemolysis ≦ 10% is considered not to be of clinical relevance. Absorbance (Abs.) is $OD_{540}$ nm.

Flocculation Assay:

The presence of precipitation or flocculation, a pellet and/or coagulation indicates that a test article is incompatible (positive test result). The absence of precipitation or flocculation, pellet and/or coagulation means the test article is compatible (negative test result).

Results

The hemolytic potential of each test article was evaluated in human whole blood. The data are presented in Table 5. None of the test articles at any concentration tested caused any hemolysis of human blood.

The compatibility of the test article in human plasma and serum was also evaluated. The data are presented in Table 6. When examined macroscopically and microscopically, no flocculation/precipitation or coagulation indicative of incompatibility was observed in any of the serum or plasma samples. On centrifugation, a pellet was observed in all tubes including the tube in which plasma was mixed with saline. The pellets were slightly red in color and probably represented small amounts of red blood cells that were present in the serum and plasma samples.

TABLE 5

Hemolysis assay in human blood.

| Treatment | Concentration | $OD_{540}$ Without blood | $OD_{540}$ with Blood | % Hemolysis |
|---|---|---|---|---|
| Saline | 0.9% | — | 0.175 | |
| | — | — | 2.495 | 100 |
| Test Article A | Undiluted | 0.057 | 0.135 | –4.18 |
| | 1:10 | 0.057 | 0.175 | –2/45 |
| | 1:20 | 0.057 | 0.173 | –2.54 |
| Test Article B | Undiluted | 0.057 | 0.193 | –1.68 |
| | 1:10 | 0.062 | 0.184 | –2.28 |
| | 1:20 | 0.057 | 0.183 | –2.11 |
| Test Article C | Undiluted | 0.058 | 0.193 | –1.72 |
| | 1:10 | 0.057 | 0.189 | –1.85 |
| | 1:20 | 0.058 | 0.184 | –2.11 |

TABLE 6

Compatibility of test articles with human plasma and serum.

| Treatment | Concentration | Plasma | | | Serum | | | Saline | | |
| | | Macro | Micro | Pellet | Macro | Micro | Pellet | Macro | Micro | Pellet |
|---|---|---|---|---|---|---|---|---|---|---|
| Saline | 0.9% | – | – | + | nd[1] | nd- | nd | nd | nd | nd |
| Test Article A | Undiluted | – | – | + | – | – | + | – | – | – |
| | 1:10 | – | – | + | – | – | + | – | – | – |
| | 1:20 | – | – | + | – | – | + | – | – | – |
| Test Article B | Undiluted | – | – | + | – | – | + | – | – | – |
| | 1:10 | – | – | + | – | – | + | – | – | – |
| | 1:20 | – | – | + | – | – | + | – | – | – |
| Test Article C | Undiluted | – | – | + | – | – | + | – | – | – |
| | | – | – | + | – | – | + | – | – | – |
| | | – | – | + | – | – | + | – | – | – |

[1] not done
+ = presence of precipitation/coagulation or a pellet
– = absence of precipitation/coagulation or a pellet

CONCLUSION

Based on the data from this study, the test articles containing dithiothreitol buffer, n-acetyl cysteine buffer, or monothioglycerol buffer were not hemolytic in human blood at any concentration tested and were compatible with human plasma and serum at all concentrations tested.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A stabilized pharmaceutical composition comprising fibroblast growth factor-2 (FGF-2), glycine and dithiothreitol (DTT) in an amount sufficient to inhibit oxidation of said FGF-2, wherein said glycine is present at a concentration of about 0.5% to about 5%, and wherein cysteine residues in said growth factor need to be maintained in a reduced state.

2. The composition of claim 1, wherein said FGF-2 lacks any disulfide bonds.

3. The composition of claim 1, wherein said composition is a liquid formulation.

4. The composition of claim 1, wherein said composition is a lyophilized formulation.

5. The composition of claim 1, wherein said FGF-2 is a biologically active fragment of FGF-2.

6. The composition of claim 1, wherein said FGF-2 is recombinant FGF-2.

7. The composition of claim 1, wherein said composition has a hemolytic potential of less than about 10%.

8. The composition of claim 1, wherein said composition has a pH within the range of about pH 3.0 to about pH 7.5.

9. The composition of claim 8, wherein said composition has a pH within the range of about pH 5.5 to about pH 6.5.

10. The composition of claim 1, wherein said DTT is present at a concentration of about 0.1 mM to about 10 mM.

11. The composition of claim 1, further comprising n-acetyl-cysteine.

12. The composition of claim 11, wherein said n-acetyl-cysteine is present at a concentration of about 0.5%.

13. The composition of claim 1, wherein said FGF-2 comprises a sequence selected from the group consisting of SEQ ID NO:1, SEQ ID NO:2, SEQ ID NO:3, or SEQ ID NO:4, or a biologically active fragment thereof.

* * * * *